US010869955B2

(12) United States Patent
Jiang et al.

(10) Patent No.: US 10,869,955 B2
(45) Date of Patent: Dec. 22, 2020

(54) JOINT FAT PAD FORMULATIONS, AND METHODS OF USE THEREOF

(71) Applicant: Allergan, Inc., Irvine, CA (US)

(72) Inventors: Guang-Liang Jiang, Irvine, CA (US); Catherine C. Turkel, Newport Coast, CA (US); Michael E. Stern, Mission Viejo, CA (US); Christopher S. Schaumberg, Huntington Beach, CA (US); Wendy M. Blanda, Tustin, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 15/540,103

(22) PCT Filed: Jan. 28, 2016

(86) PCT No.: PCT/US2016/015384
§ 371 (c)(1),
(2) Date: Jun. 27, 2017

(87) PCT Pub. No.: WO2016/123352
PCT Pub. Date: Aug. 4, 2016

(65) Prior Publication Data
US 2017/0368236 A1 Dec. 28, 2017

Related U.S. Application Data

(60) Provisional application No. 62/108,696, filed on Jan. 28, 2015, provisional application No. 62/108,709, filed on Jan. 28, 2015.

(51) Int. Cl.
*A61L 31/04* (2006.01)
*A61L 31/14* (2006.01)
*A61L 31/16* (2006.01)

(52) U.S. Cl.
CPC .......... *A61L 31/042* (2013.01); *A61L 31/145* (2013.01); *A61L 31/16* (2013.01); *A61L 2300/402* (2013.01); *A61L 2300/41* (2013.01); *A61L 2300/426* (2013.01); *A61L 2300/43* (2013.01); *A61L 2300/622* (2013.01); *A61L 2300/624* (2013.01); *A61L 2400/06* (2013.01); *A61L 2430/24* (2013.01)

(58) Field of Classification Search
CPC ..... A61P 19/02; A61K 9/0024; A61K 31/573; A61K 31/728; A61K 47/26; A61L 27/48; A61L 27/52; A61L 31/042
See application file for complete search history.

(56) References Cited

U.S. PATENT DOCUMENTS

| 7,189,392 | B1 * | 3/2007 | Kim ................. A61K 9/0019 424/94.1 |
| 7,662,409 | B2 | 2/2010 | Masters |
| 7,910,123 | B2 | 3/2011 | McKay |
| 8,784,893 | B2 | 7/2014 | Daniloff et al. |
| 8,962,666 | B2 | 2/2015 | Emans et al. |
| 2002/0111603 | A1 | 8/2002 | Cheikh |
| 2003/0148995 | A1 | 8/2003 | Piron et al. |
| 2006/0122147 | A1 * | 6/2006 | Wohlrab ............ A61K 31/728 514/54 |
| 2006/0194758 | A1 | 8/2006 | Lebreton |
| 2007/0178138 | A1 | 8/2007 | Pal et al. |
| 2007/0203095 | A1 | 8/2007 | Sadozai et al. |
| 2008/0089918 | A1 | 4/2008 | Lebreton |
| 2008/0293919 | A1 | 11/2008 | Kaplan et al. |
| 2010/0015196 | A1 | 1/2010 | Kimble et al. |
| 2010/0028438 | A1 | 2/2010 | Lebreton |
| 2010/0215731 | A1 | 8/2010 | Emans et al. |
| 2010/0226988 | A1 | 9/2010 | Lebreton |
| 2011/0052695 | A1 | 3/2011 | Jiang et al. |
| 2011/0077737 | A1 | 3/2011 | Stroumpoulis et al. |
| 2011/0111031 | A1 | 5/2011 | Jiang et al. |
| 2013/0096081 | A1 | 4/2013 | Njikang et al. |
| 2014/0038917 | A1 * | 2/2014 | Gavard Molliard ........ A61K 31/728 514/54 |

(Continued)

FOREIGN PATENT DOCUMENTS

| WO | 2004073759 A1 | 9/2004 | |
| WO | WO-2013076160 A1 * | 5/2013 | ........... A61K 9/0019 |

OTHER PUBLICATIONS

Slomkowski, S. et al "Terminology of polymers and polymerization . . . " Pure Appl. Chem., vol. 83, No. 2, pp. 2229-2259 (Year: 2011).*
Grecomoro, G. et al "Therapeutic synergism between hyaluronic acid and dexamethasone . . . " Curr. Med. Res. Opin., vol. 13, No. 1, pp. 49-55. (Year: 1992).*
Gerwin, N. et al "Intraarticular drug delivery in osteoarthritis" Adv. Drug Deliv. Rev., vol. 58, pp. 226-242. (Year: 2006).*
Yadav, A. et al "An insight on hyaluronic acid in drug targeting . . . " J. Drug Targeting, vol. 16, No. 2, pp. 91-107. (Year: 2008).*
Arthur S. Tatham and Peter R. Shewry, Comparative Structures and Properties of Elastic Proteins, The Royal Society, Feb. 28, 2002, 229-234, 357, Phil. Trans. R. Soc. London, London, GB.

(Continued)

Primary Examiner — Leigh C Maier
(74) Attorney, Agent, or Firm — Lorenz Siddiqi

(57) ABSTRACT

The present invention relates to formulations for administration to a joint fat pad of a subject, and to methods of treating joint pain, inflammation or disease. The disclosed formulations are intended for local administration to the joint fat pad to provide sustained release of a therapeutic agent to the joint cavity and surrounding tissues. The joint may be an arthritic joint, an injured joint or a surgically replaced joint. The therapeutic agent may be an analgesic agent, an anti-inflammatory agent or an immunosuppressive agent. A single administration of the formulation to the joint fat pad delivers a therapeutically effective amount of the therapeutic agent with reduced systemic exposure relative to a single systemic or a single intra-articular administration of a therapeutic dose of an identical therapeutic agent.

16 Claims, 6 Drawing Sheets

(56) References Cited

U.S. PATENT DOCUMENTS

2014/0088038 A1 3/2014 Su et al.
2015/0086531 A1 3/2015 Jiang

OTHER PUBLICATIONS

Borja, Maria J. et al., Prefemoral Fat Pad Impingement Syndrome: Indentification and Diagnosis, The American Journal of Orthopedics, Jan. 2013, pp. E9-E11.
Chuckpaiwong, Bavornrit et al., Age-Associated Increases in the Size of the Infrapatellar Fat Pad in Knee Osteoarthritis as Measured by 3T MRI, Journal of Orthopaedic Research, Sep. 2010, pp. 1149-1154, 28, Wiley Periodicals, Inc.
Claus Larsen et al., Intra-Articular Depot Formulation Princilples: Role in the Management of Postoperative Pain and Arthritic Disorders, Journal of Pharmaceutical Sciences, Nov. 2008, pp. 4622-4654, vol. 97, No. 11.
Distel, Emile et al., The Infrapatellar Fat Pad in Knee Osteoarthritis an Important Source of Interleuki-6 and Its Soluble Receptor, Arthritis & Rheumatism, Nov. 2009, pp. 3374-3377, vol. 60, No. 11, American College of Rheumatology.
Erdemli, Ozge et al., In vitro evaluation of effects of sustained anti-TNF release from MPEG-PCL-MPEG and PCL microspheres on human rheumatoid arthritis synoviocytes, Journal of Biomaterials Applications, 2014, pp. 524-542, vol. 29, 4.
Gerwin, Nicole et al., Intraarticular drug delivery in osteoarthritis, Advanced Drug Delivery Reviews, 2006, pp. 226-242, vol. 58, Elsevier.
Heller, Jorge, Biodegradable Polymers in Controlled Drug Delivery, CRC Critical Reviews in Therapeutic Drug Carrier Systems, 1987, 39-90, 1(1).
Patent Cooperation Treaty, Notification of Transmittal of the International Search Report and the Written Opinion of the International Searching Authority, or the Declaration, dated May 4, 2016, pp. 11.
Petit, Audrey et al., Release behavior and intra-articular biocompatibility of celecoxib-loaded acetyl-capped PCLA-PEG-PCLA thermogels, Biomaterials, 2014, pp. 7919-7928, vol. 35, Elsevier Ltd.
Shabshin, Nogah et al., Quadriceps fat pad edema: significance on magnetic resonance images of the knee, Skeletal Radiol , 2006, pp. 269-274, vol. 35, 5.
Staeubli, Hans-Ulrich et al., Qunatification of Intact Quadriceps Tendon, Quadriceps Tendon Insertion, and Suprapatellar Fat Pad: MR Arthrography, Anatomy, and Cryosections in the Sagittal Plane, AJR, Sep. 1999, pp. 691-698, 173, American Roentgen Ray Society.
Tsavalas, Nikolaos et al., Suprapatellar Fat-Pad Mass Effect: MRI Findings and Correlation With Anterior Knee Pain, Musculoskeletal Imaging * Original Research, Mar. 2013, pp. W291-W296, AJR:200.
Yang, Xiaoye et al., Progress in Intra-Articular Drug Delivery Systems for Osteoarthritis, Current Drug Targets, 2014, pp. 888-900, 15.

* cited by examiner

The infrapatellar fat pad is a favorable site for delivering sustained release drug to the synovium

| Treatment | | | No Treatment | | Placebo | | 2% Dex·HA Gel IF | | 10% Dex·HA Gel IF | | 20% Dex·HA Gel IF | | DEX IF | | DEX IA | |
|---|---|---|---|---|---|---|---|---|---|---|---|---|---|---|---|---|
| Matrix | Day | Location | Mean | SD | Mean | SD | Mean | SD | Mean | SD | Mean | SD | Mean | SD | Mean | SD |
| Fat Pad (ng) | 1 | Lateral | 0 | 0 | 0 | 0 | 0 | 0 | 194859 | 279321 | 2694291 | 2136859 | 8.41 | 6.7 | 1.36 | 0.45 |
| | 1 | Medial | 0 | 0 | 0 | 0 | 0 | 0 | 6251 | 16426 | 35211 | 59982 | 12.1 | 11.6 | 1.54 | 0.36 |
| Plasma (ng/ml) | 1 | | 0 | 0 | 0 | 0 | 0 | 0 | 2.05 | 2.78 | 6.95 | 4.8 | 0 | 0 | 0 | 0 |
| Synovial Fluid (ng/mL) | 1 | Left | 0 | 0 | 0 | 0 | 0 | 0 | 717 | 1797 | 106 | 102 | 0 | 0 | 0 | 0 |
| | 1 | Right | 0 | 0 | 0 | 0 | 0 | 0 | 1.43 | 1.89 | 3.65 | 2.76 | 0 | 0 | 0 | 0 |

Day-7 injection: Placebo, 2% Dex·HA Gel IF, 10% Dex·HA Gel IF, 20% Dex·HA Gel IF
Day-1 injection: DEX IF, DEX IA

FIG. 6

JOINT FAT PAD FORMULATIONS, AND METHODS OF USE THEREOF

CROSS-REFERENCE TO RELATED APPLICATIONS

This application is a national stage application filed under 35 U.S.C. § 371 of International Patent Application Serial No. PCT/US2016/015384, filed on Jan. 28, 2016, which claims priority to and the benefit of U.S. Provisional Application Ser. No. 62/108,696 filed on Jan. 28, 2015, and U.S. Provisional Application Ser. No. 62/108,709 filed on Jan. 28, 2015, each of which is hereby incorporated in its entirety by this specific reference.

FIELD OF THE INVENTION

The invention relates generally to formulations to treat pain, inflammation or disease in a subject. More specifically, the invention relates to formulations for local administration to a joint fat pad of a subject, the formulations providing sustained release of a therapeutic agent to the joint cavity and surrounding tissues. The invention further relates to methods of treating pain or inflammation in a subject with arthritis, autoimmune disease, post-operative pain or a surgically replaced joint by administering a sustained release formulation to a joint fat pad of the subject.

BACKGROUND OF THE INVENTION

Arthritis is one of the most prevalent chronic health problems and common causes of disability, affecting over 45 million adults in the United States. This number is anticipated to rise to 60 million, or 18% of the population, by 2020. The Arthritis Foundation describes arthritis as a complex family of musculoskeletal disorders including more than 100 different diseases or conditions that destroy joints, bones, muscles, and other connective tissues, hampering or halting physical movement. Osteoarthritis (OA) is the most common form of arthritis and a leading cause of disability among adults over the age of 65. Also known as "degenerative joint disease," OA may result from cumulative joint wear and tear, or from joint trauma or injury. Rheumatoid arthritis (RA) is an autoimmune form of arthritis, generally affecting the joints of the knees, hands and elbows of people over the age of 20. Regardless of the type of arthritis, common symptoms for all arthritic disorders include varied levels of pain, swelling, functional limitation and joint stiffness.

In addition to OA and RA, there are more than 100 arthritic diseases and conditions defined by the Arthritis Foundation, including ankylosing spondylitis, calcium pyrophosphate dehydrate crystal deposition disease (CPPD, or pseudo gout), Ehlers-Danlos syndrome, fibromyalgia, fifth disease, giant cell arteritis, gout, juvenile arthritis, lyme arthritis, myositis, psoriatic arthritis, Raynaud's phenomenon, reactive arthritis (Reiter's syndrome), reflex sympathetic dystrophy syndrome, Sjögren's syndrome, Still's disease, systemic lupus, and tendinitis. Some arthritic conditions are secondary to other diseases or conditions.

The goals of current therapies for arthritis, including OA, are to alleviate pain and other related arthritis associated symptoms. Current therapies for managing OA pain include oral analgesics or corticosteroids, localized treatments with topical analgesics (e.g., NSAIDs, capsaisin), and intra-articular injections of corticosteroids or viscosupplements. Oral analgesics have substantial limitations because they may not provide sufficient pain relief and often produce intolerable side effects, for example, gastrointestinal bleeding and renal toxicity for regular NSAID users, addiction or breathing suppression for opioids, and adverse drug interactions. Localized corticosteroid injections may reduce pain for a short period (1-3 weeks), but have long term side effects after repeated bolus injections, including cartilage break down or Cushing's syndrome; furthermore, they are intolerable to patients with diabetic mellitus. Viscosupplement administration, such as hyaluronic acid, while well-tolerated, is not always effective.

The chronic nature of arthritis often requires treatment for extended periods of time. It is generally known that local administration of a therapeutic agent can offer benefits over modes of administration that result in systemic exposure. The benefits of local administration include enhancements in local efficacy and/or reductions in side effects associated with exposure of organs or tissues to the agent where the agent provides no benefit and/or may induce harm. In this way, the local administration of an agent may improve the therapeutic index of the agent while mitigating the risks of systemic effects. This is particularly beneficial for chronic conditions, such as OA.

Patients suffering from arthritis are generally treated with a combination of systemic and/or local formulations to manage inflammation and pain during disease progression. Local drug delivery to the affected joint may be used to reduce inflammation and pain in patients, while mitigating the risk of systemic side effects. Several compounds and delivery methods have been investigated and used to treat disease locally, in both animals and human subjects, with varying degrees of success (Larson et al., Intra-articular depot formulation principles: role in the management of postoperative pain and arthritic disorders, *J Pharm Sci*, 97(11), pp. 4622-4654, 2008). Methods to enhance efficacy and increase the duration of the therapeutic effect, and thereby minimize the number of injections, are a major focus of investigation, and a top priority for new treatment modalities.

A fat pad (*Corpus adiposum* or "fat body") comprises an accumulation of encapsulated adipose tissue. The adipose tissue comprises closely packed fat cells and is generously supplied with capillaries and nerve endings. Intra-articular fat pads (fat pads situated within joints) are surrounded by a porous synovial membrane. The fat pad may assist in the spreading of synovial lubricant to the joint. Given the location, function, and in some cases, the volume, of joint fat pads, the pathological role of fat pads (for example, in OA), and the porosity of the surrounding synovial membrane, the fat pad may serve as a location for the injection of sustained release drug delivery formulations, and for facilitating drug diffusion from the fat pad-embedded drug delivery system to the joint cavity in subjects with arthritis. The local delivery of the drug may minimize undesirable affects associated with systemic exposure.

Intra-articular fat pads are associated with joints including but not limited to the knee, ankle (Kager's fat pad), foot (e.g., plantar fat pad), elbow, hand and hip (i.e., the acetabulum). The knee has three major anterior fat pads: the infrapatellar, suprapatellar, and prefemoral fat pads (FIG. 1). The infrapatellar fat pad (also known as Hoffa's fat pad) is located superior to the tibia, and right below the inferior surface of the patella and underneath the patellar ligament. It resides inside the knee capsule and is separated from the joint cavity by a single layer of synovial membrane. The infrapatellar fat pad weighs approximately 20 grams in Europeans and its volume is about 22 cubic centimeters. The volume of the fat pad has a positive association with age in knee OA patients, but not in normal control patients (Chuckpaiwong et al., Age-associated increases in the size of the infrapatellar fat pad in knee osteoarthritis as measured by 3T MRI. *J Orthopaedic Research*, 28, pp. 1149-1154, 2010). Interestingly, the infrapatellar fat pad of knee OA patients synthesizes and releases two-fold greater interleukin-6 (IL-6) and 3.6-fold greater IL-6 soluble receptor than corresponding normal subcutaneous fat tissue (Distel et al., The infrapatellar fat pad in knee osteoarthritis: an important source of interleukin-6 and its soluble receptor, *Arthritis & Rheumatism*, 60, pp. 3374-3377, 2009). It is known that IL-6 and other inflammatory cytokines play important roles in the pathogenesis of knee OA and pain. It is thought that the fat pad may be a source of knee pain because of its enrichment of sensitive nerve fibers, especially in the anterior region of the knee. Furthermore, the synovial membrane, which isolates the fat pad from the knee cavity, consists of intimal cells and matrix and is enriched with vascular net and nerve fibers. The synovial membrane has a porosity which allows solutes as large as proteins to pass without significant hindrance.

The present invention provides sustained release formulations for administration to the fat pad of a joint, providing local delivery of a therapeutic agent to the joint of a subject. The invention further provides for methods of treating a disease or condition in a subject, wherein the disease or condition is arthritis, autoimmune disease (including rheumatoid arthritis), pain, inflammation, and combinations thereof. The joint may be an arthritic joint, an injured joint, or a surgically replaced joint. The provided method comprises administering a formulation to at least one joint fat pad of the subject, the formulation comprising a therapeutic agent selected from analgesics, anti-inflammatory agents, immunosuppressive agents, and combinations thereof. The administered formulation provides sustained release of the therapeutic agent to the joint cavity, surrounding tissues, or both, of the subject in need of the treatment, with minimal systemic exposure to the subject.

SUMMARY OF THE INVENTION

Disclosed herein are formulations and methods for treating arthritis, autoimmune disease, pain, inflammation, and combinations thereof, in a subject in need of such treatment, with minimal systemic exposure to the subject.

Aspects of the present disclosure provide for sustained release formulations for administration to a joint fat pad of a subject, and for their use in treating a variety of conditions, such as arthritis, autoimmune disease, pain and/or inflammation. The formulations comprise one or more therapeutic agents. The formulations can be administered to one or more joint fat pads of the subject. The administration may be performed by way of injecting, implanting, or embedding the formulation into one or more joint fat pads. The pain and inflammation that may be treated by the formulations and methods of the invention can be associated with arthritis, including osteoarthritis and rheumatoid arthritis, post-operative pain, joint replacement surgery pain, and the like. The invention further provides for sustained release of the therapeutic agent to the joint or surrounding tissues with improved efficacy and/or reduced systemic exposure.

In one aspect of the invention, there is provided a formulation for administration to a joint fat pad of a subject, the formulation comprising a therapeutic agent selected from an analgesic agent, an anti-inflammatory agent, an immunosuppressive agent, and combinations thereof. In further aspects, the formulation provides sustained release of the therapeutic agent to the joint, including the joint cavity and surrounding tissues.

In another aspect of the invention, there is provided a formulation for administration to a joint fat pad of a subject, the formulation providing a therapeutically effective amount of the therapeutic agent, thereby relieving the joint from pain, inflammation or disease.

In other aspects of the invention, there is provided a formulation for administration to an arthritic joint, an injured joint or a surgically replaced joint.

In yet other aspects of the invention, there is provided a formulation for administration to the infrapatellar fat pad of a knee joint.

In other aspects of the invention, there is provided a formulation for administration to a fat pad, the formulation comprising an anti-inflammatory agent such as dexamethasone.

In some aspects, the formulation is provided as a gel suspension. In other aspects, the formulation is provided as a solid or semi-solid implant.

In other aspects, the invention provides a method of treating pain, inflammation, or disease in a joint of a subject in need of such treatment, the method comprising administering a sustained release formulation as disclosed herein to a fat pad of the joint of the subject.

In other aspects, the invention provides for a method of treating pain, inflammation, or disease in a knee joint of a subject, the method comprising administering the formulation to an infrapatellar fat pad of the knee joint of the subject.

In further aspects, the invention provides for a method of treating an arthritic joint, an injured joint or a surgically replaced joint in a subject, the method comprising injecting, embedding, or implanting the sustained release formulation into a fat pad of the joint of the subject.

In some aspects, the invention provides for a method of treating joint pain, inflammation or disease associated with osteoarthritis, rheumatoid arthritis, juvenile arthritis, calcium pyrophosphate dehydrate crystal deposition disease (CPPD, or pseudo gout), post-operative pain, joint replacement surgery pain or a combination thereof, in a subject, the method comprising administering the formulation to a fat pad of the joint of the subject.

In other aspects, the invention provides a method of treating joint pain, inflammation or disease in a subject, comprising administration of the sustained release formulation to the joint fat pad, the method providing at least one of reduced systemic exposure, reduced side effects, enhanced dosing precision, and reduced frequency of administration; wherein each reduction or enhancement is relative to a systemic or intra-articular administration of a therapeutic dose, such as a routine therapeutic dose, of an identical therapeutic agent.

In other aspects, the invention provides a method of treating joint pain, inflammation and/or disease in a subject, the method comprising a single administration of the sustained release formulation to the joint fat pad, wherein the single administration to the joint fat pad is sufficient to provide a therapeutically effective amount of a therapeutic agent to the joint, thereby relieving the joint from the pain, inflammation or disease. In further aspects, the single administration of the formulation to the joint fat pad delivers the therapeutically effective amount of the therapeutic agent with reduced systemic exposure and/or reduced side effects relative to a single systemic or a single intra-articular administration of a therapeutic dose, such as a routine therapeutic dose, of an identical therapeutic agent. In yet further aspects, the single administration of the formulation to the joint fat pad provides equivalent or superior relief of pain, inflammation and/or disease of the joint relative to a single systemic or intra-articular administration of a therapeutic dose, such as a routine therapeutic dose, of the therapeutic agent.

Additional aspects and advantages of the present invention are set forth in the following description and claims, particularly when considered in conjunction with the accompanying drawings.

BRIEF DESCRIPTION OF THE DRAWINGS

FIG. 5 shows the results of efficacy studies of infrapatellar fat pad delivery of sustained release dexamethasone gel suspension (depot) compared to dexamethasone sodium phosphate injection.

FIG. 6 shows local and systemic pharmacokinetics of gel suspension (depot) formulations containing dexamethasone (Dex:HA) versus injection of dexamethasone sodium phosphate injection (Dex) delivered intra-fat pad or intra-articularly. Drug concentrations (determined by HPLC) in the fat pad, blood plasma and synovial fluid of rabbits treated with Dex:HA gel suspensions or Dex.

DETAILED DESCRIPTION OF THE INVENTION

Figure 1:
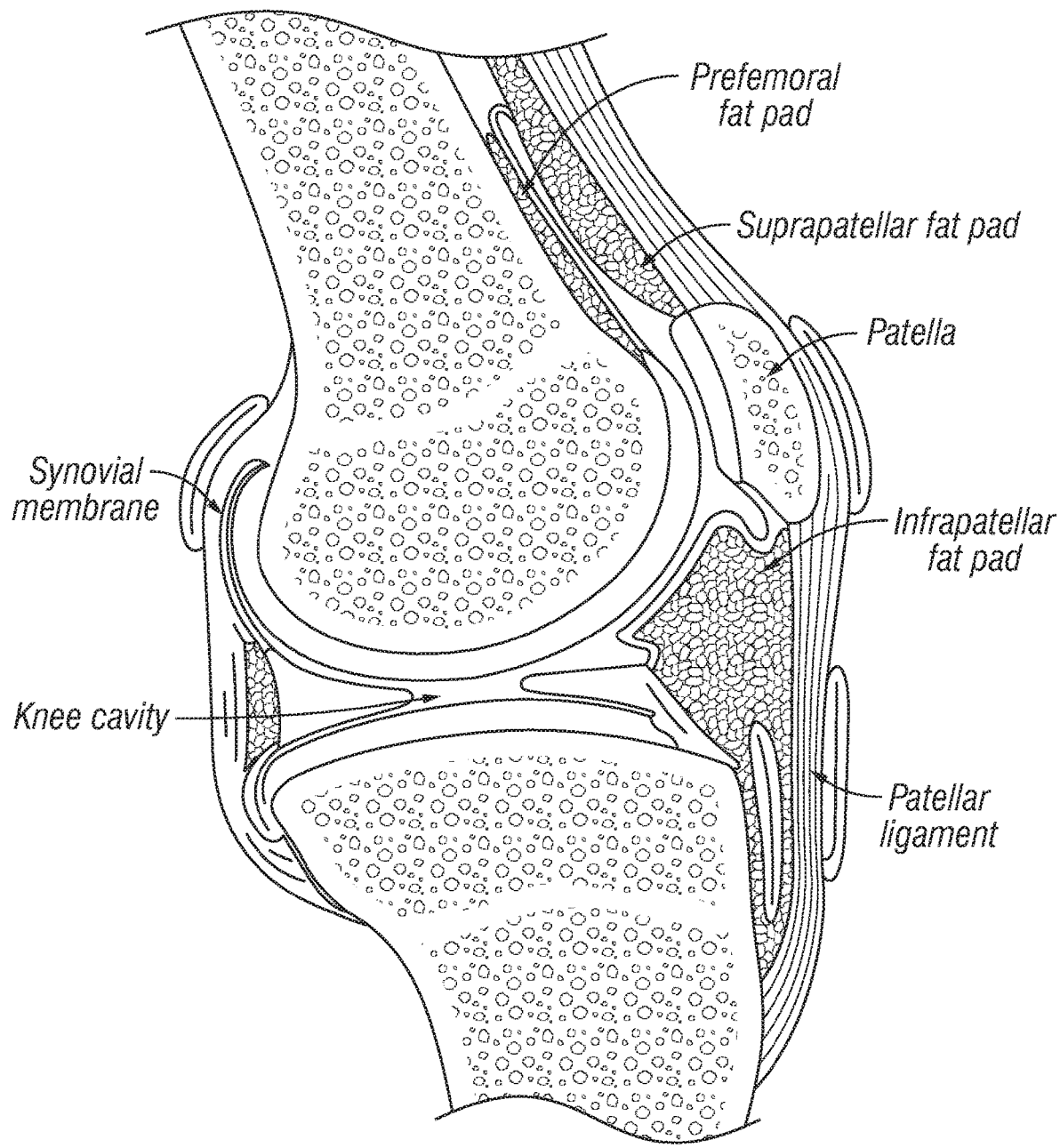
FIG. 1 shows the anatomical structure of the knee, including the locations of the infrapatellar fat pad, suprapatellar fat pad, and prefemoral fat pad.

In some aspects, the present disclosure provides for sustained release formulations for administration to a joint fat pad of a subject. In other aspects, the disclosure provides for methods of treating arthritis, autoimmune disease, pain, inflammation, and the like, in a subject in need of such treatment. In further aspects, the present disclosure provides for methods for treating pain and/or inflammation associated with OA, RA, post-operative pain, joint replacement surgery pain, and the like.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Arthritis. Arthritis is a form of joint disorder that involves inflammation of one or more joints. Normal articular cartilage consists of an extensive hydrated extracellular matrix. The matrix consists mainly of collagen and proteoglycans, principally aggrecan, which is large and aggregates with hyaluronic acid. Embedded in the extracellular matrix are the chondrocytes, which regulate the synthesis and degradation of the articular cartilage. In normal articular cartilage, the extracellular matrix is constantly being degraded and synthesized. Collagen and cartilage proteoglycans are degraded by various proteinases, including metalloproteinases and collagenages. Under normal circumstances, the activation of these degradative enzymes is held in check by inhibitors, such as tissue inhibitor of metalloproteinases (TIMPs) and plasminogen activator inhibitor-7 (PAI-7). The balance of metalloproteinases (MMPs) and inhibitors of metalloproteinases (TIMPs) is important to maintain the normal turnover of the extracellular matrix. Under pathological conditions such as for example in OA and RA, mechanical and shear stress, inflammatory cytokines (e.g., IL-1, IL-6 and tumor necrosis factor-$\alpha$) and/or growth factors disrupt this balance and promote the synthesis of MMPs and inhibit the expression of TIMPs. Thus, collagen and aggrecan degradation will outweigh the synthesis and deposition by chondrocytes, which ultimately results in cartilage defect. Inflammation can occur secondary to structural damage as in osteoarthritis or is the main cause to incur arthritis with subsequent structural damage as in rheumatoid arthritis.

Osteoarthritis. OA is the most common form of arthritis and a leading cause of chronic disability. It can affect both the larger and the smaller joints of the body, including the hands, feet, back, hip, knee and spine. OA is a multifactorial disease, characterized by joint pain, tenderness, limitation of movement, crepitus, occasional effusion, wear or tear of cartilage, wear or tear of meniscus, wear or tear of ligament, subchondrial bone lesion, capsule damage and/or hyperplasia of the synovial membrane. Progression of OA is marked by destruction of the joint cartilage, sclerosis or cyst formation of underlying bone, joint space narrowing and formation of osteophytes at the joint margin.

Rheumatoid Arthritis. RA is an autoimmune disease that results in a chronic, systemic inflammatory disorder that may affect many tissues and organs, but principally attacks flexible (synovial) joints. It can be a disabling and painful condition, which can lead to substantial loss of functioning and mobility if not adequately treated. Joint cartilage loss and other structural damage is subsequent to inflammatory response at the involved joints. Once cartilage lesion occurs, RA will have a similar disease progression as OA even after the primary inflammation cause is under control.

Definitions

As used herein, the words or terms set forth below have the following definitions:

"About" or "approximately" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value.

"Administration" or "to administer" means the step of giving (i.e. administering) a formulation to a subject, or alternatively a subject receiving a therapeutic agent. As used herein, the term "administering" means any delivery mechanism that provides a composition disclosed herein to an individual that potentially results in a clinically, therapeutically, or experimentally beneficial result. The present method can be performed via administration routes including intra-fat pad injection, intra-articular injection, extra-articular injection, peri-articular injection, bolus injection (for example, of a gel suspension into a fat pad), implantation (for example, of a slow-release polymeric implant into a fat pad), or combinations thereof.

"Alleviating" means a reduction in pain, inflammation and/or disease-associated condition. Thus, alleviating includes some reduction, significant reduction, near total reduction, and total reduction.

"Anterior knee fat pad" as used herein, includes the infrapatellar fat pad, the suprapatellar fat pad, and/or the prefemoral fat pad. The infrapatellar fat pad (Hoffa's fat pad) is located superior to the tibia, and right below the inferior surface of the patella and underneath the patellar ligament. The suprapatellar fat pad is located just above the patella and directly behind the quadriceps tendon, and is generally constant in shape and size. The prefemoral fat pad is located just anterior to the femur, is variable in size and shape, ranging from flat to plump. The surpapatellar bursa extends up between the suprapatellar fat pad and the prefemoral fat pad. When the surpapatellar bursa contains little fluid, the bursa is essentially a potential space only, and the surpapatellar fat pad and the prefemoral fat pad are separated by less than 5 mm. When suprapatellar effusion occurs, the two fat pads may be pushed apart by the effusion to a distance of 5 mm or greater.

"Biodegradable polymer" and "bioerodible polymer" are equivalent and are used interchangeably herein. "Biodegradable polymer" refers to a polymer or polymers which degrade in vivo, and wherein erosion of the polymer or polymers over time occurs concurrent with or subsequent to release of the therapeutic agent. A biodegradable polymer may be a homopolymer, a copolymer, or a polymer comprising more than two different polymeric units.

"Extra-articular injection" refers to an injection outside of a joint space.

"Formulation" and "composition" may be used interchangeably and refer to a combination of elements that is presented together for a given purpose. Such terms are well known to those of ordinary skill in the art.

"Implant" means a controlled release (e.g., pulsatile or continuous) composition or drug delivery system. The implant can be, for example, injected, inserted or implanted into a human body, for example, into a joint fat pad.

"Intra-articular injection" refers to an injection directly into a joint or into a portal.

"Intra-fat pad injection" refers to an injection directly into a fat pad.

"Joint fat pad" refers to a fat pad associated with a joint. For example, knee fat pad refers to one or more of the fat pads associated with the knee.

"Liposomes" refers to a vesicle composed of one or more bilayer membranes formed of naturally-derived phospholipids with mixed lipid chains or of pure surfactant components.

Liposomes, usually but not by definition, contain a core of aqueous solution.

"Local administration" means administration of a therapeutic agent to the vicinity of an affected site in a subject by a non-systemic route. Thus, local administration excludes systemic routes of administration, such as intravenous or oral administration.

"Mammal" means humans and other mammalian animals.

"Micelle" refers to an aggregate of surfactant molecules dispersed in a liquid colloid.

"Microsphere" and "nanosphere" each refer to a spherical shell that is usually made of a biodegradable or resorbable polymer, that has a very small diameter usually in the micron or nanometer range, respectively, and that is often filled with a therapeutic agent for release as the shell is degraded.

"Patient" or "subject" refers to both humans and mammalian animals.

"Peri-articular injection" refers to an injection to an area around a joint.

"Pharmaceutically acceptable" means any molecular entity or composition that does not produce an adverse, allergic or other untoward or unwanted reaction when administered to an individual subject.

"Routine therapeutic dose" refers to a therapeutic dose administered in an amount sufficient to achieve a desired therapeutic effect as routinely determined by a clinician, medical doctor, veterinarian or other qualified practitioner. The routine therapeutic dose usually refers to the amount routinely administered per injection site per patient treatment session, most usually as used according to an approved label.

"Steroidal anti-inflammatory agents" include steroidal compounds or drugs which reduce inflammation when administered at a therapeutically effective level.

"Sustained" as in "sustained period" or "sustained release" means for a period of time of at least about a day, about two days, about three days, about 4 days, about 5 days, about six days, about 7 days, about 8 days; or at least about one week, about two weeks, about three weeks, about four weeks; or at least about one month, about two months, about three months, about four months, about five months, about six months, about seven months, about eight months, about nine months, about ten months, about 11 months, about 12 months; or at least about a year or more, unless expressly defined otherwise.

"Therapeutic agent" means a substance that will elicit the biological or medical response of a subject in need thereof that is being sought by the researcher, veterinarian, medical doctor or other clinician.

"Therapeutic dose" refers to an amount sufficient to achieve a desired therapeutic effect. The therapeutic dose usually refers to the amount administered per injection site per patient treatment session, unless indicated otherwise.

"Therapeutically effective amount" refers to an amount sufficient to achieve a desired therapeutic effect. The therapeutically effective amount usually refers to the amount administered per injection site per patient treatment session, unless indicated otherwise.

"Treat", "treating" or "treatment" means to alleviate (or to eliminate) an undesirable condition either temporarily or permanently, for example, pain or inflammation associated with arthritis, or post-operative pain.

As can be appreciated from the present invention, the therapeutic agent of the sustained release formulation can be released from the formulation, and can be associated with reduced systemic exposure, reduced side effects, enhanced dosing precision, and/or reduced frequency of administration relative to a systemic or intra-articular administration of a therapeutic dose, such as a routine therapeutic dose, of an identical therapeutic agent.

As can be further appreciated, a single administration of the sustained release formulation to a joint fat pad may provide equivalent or superior relief of pain, inflammation and/or disease of the joint relative to a single systemic or intra-articular administration of a therapeutic dose, such as a routine therapeutic dose, of the same therapeutic agent. The superior efficacy provided by administration of the sustained release formulation to the joint fat pad may be attributed to its ability to provide a high local therapeutic drug concentration and/or to maintain a sustained and constant therapeutic drug concentration, which are not achievable by systemic bolus delivery. In further aspects, it can be appreciated that a single administration of the formulation to a joint fat pad may provide reduced systemic exposure and equivalent or superior relief of pain, inflammation and/or disease of the joint relative to a single systemic or intra-articular administration of a therapeutic dose, such as a routine therapeutic dose, of the therapeutic agent.

In one aspect of the invention, there is provided a formulation for administration to a joint fat pad of a subject, the formulation comprising a therapeutic agent selected from an analgesic agent, an anti-inflammatory agent, an immunosuppressive agent, and combinations thereof. Non-limiting examples of therapeutic agents that may be incorporated into formulations of the invention are described below.

Analgesics. Analgesics refer to agents that provide relief from pain by acting on the peripheral or central nervous system. Major classes of analgesics that can be used in formulations of the present invention include, but are not limited to, acetaminophen (paracetamol) and non-steroidal anti-inflammatory drugs (NSAIDS), steroidal anti-inflammatory drugs, cyclooxygenase-2 (COX2 inhibitors), opiates, N-Methyl-D-aspartate receptor (NMDA) receptor antagonists, and agents that are used to treat neuropathic pain.

Anti-inflammatory agents. Anti-inflammatory agents that can be used in formulations of the present invention include, but are not limited to, steroidal anti-inflammatory agents, non-steroidal anti-inflammatory agents (NSAIDs), anti-inflammatory cytokines, antimetabolites, N-Methyl-D-aspartate (NMDA) receptor antagonists, and combinations thereof.

Anti-inflammatory cytokines. Anti-inflammatory cytokines are immunoregulatory molecules that regulate the proinflammatory cytokine response. Cytokines act together with specific cytokine inhibitors and soluble cytokine receptors to regulate immune response. Anti-inflammatory cytokines that can be used in formulations of the present invention include, but are not limited to, antagonists of interleukin (IL) receptors IL-1, IL-4, IL-6, IL-11, and IL-13, and pro-inflammatory cytokine inhibitors such as tumor necrosis factor-alpha (TNF-α) and IL-18.

Antimetabolites. Antimetabolites interfere with one or more enzymes or the reactions of those enzymes that are necessary for DNA synthesis. An antimetabolite affects the synthesis of DNA by acting as a substitute for the actual metabolite that would be used in the normal metabolism. Nonlimiting examples of antimetabolites include antifolates, which interfere with the use of folic acid.

Non-steroidal anti-inflammatory agents (NSAIDS) and COX-2 inhibitors. Non-steroidal anti-inflammatory drugs that can be used in formulations of the present invention include, but are not limited to, aspirin, diclofenac, diflunisal, etodolac, ibuprofen, indomethacin, ketoprofen, ketorolac, nabumetone, naproxen, oxaprozin, piroxicam, salsalate, sulindac, tolmetin, and agents that selectively block cyclooxygenase-2 (COX-2), i.e., COX-2 inhibitors, such as celecoxib, valdecoxib and rofecoxib.

Steroidal anti-inflammatory agents. Examples of steroidal anti-inflammatory agents that can be used in formulations of the present invention include, but are not limited to, 21-acetoxypregnenolone, alclometasone, alclometasone dipropionate, algestone, amcinonide, beclomethasone, betamethasone, betamethasone dipropionate, betamethasone sodium phosphate, betamethasone valerate, budesonide, chloroprednisone, ciclesonide, clobetasol, clobetasol-17-propionate, clobetasone-17-butyrate, clobetasone, clocortolone, cloprednol, corticosterone, cortisone, cortisone acetate, cortivazol, deflazacort, desonide, desoximetasone, dexamethasone, dexamethasone sodium phosphate, diflorasone, diflucortolone, difluprednate, enoxolone, fluazacort, flucloronide, flumethasone, fluocinonide, fluocinolone, fluocinolone acetonide, fluocinonide, fluocortin butyl, fluocortolone, fluocortolone caproate, fluocortolone pivalate, fluorometholone, flunisolide, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, hydrocortisone acetate, hydrocortisone-17-aceponate, hydrocortisone-17-buteprate, hydrocortisone-17-butyrate, hydrocortisone-17-valerate, loteprednol, mazipredone, medrysone, meprednisone, methylprednisolone, mometasone, mometasone furoate, paramethasone, paramethasone acetate, prednicarbate, prednisolone, prednisolone 25-diethylamino-acetate, prednisolone sodium phosphate, prednisone, prednival, prednylidene, rimexolone, tixocortol, tixocortol pivalate, triamcinolone, triamcinolone acetonide, triamcinolone alcohol, triamcinolone benetonide, triamcinolone hexacetonide, derivatives of the foregoing, salts of the foregoing, and mixtures of the foregoing.

Opiates. Opiates or opioids are narcotic analgesics that directly depress the central nervous system. Nonlimiting examples of opiates that can be used in formulations of the present invention include codeine, morphine, dihydromorphine, fentanyl, hydrocodone, oxycodone, pethidine, methadone, dextropropoxyphene, buprenorphine, tramadol and ketobemidone.

Immunosuppressant agents. Immunosuppressant agents that inhibit or prevent immune system activity can be used in formulations of the present invention, including, but not limited to, cyclosporins (such as cyclosporine A, and analogs thereof), azathioprine (AZA), mizoribine, and tacrolimus.

N-Methyl-D-aspartate receptor antagonists. NMDA receptor antagonists are a class of anesthetics that inhibit the action of the N-Methyl-D-aspartate receptor. NMDA receptor antagonists induce a state of anesthesia known as dissociative anesthesia characterized by catalepsy, amnesia, and analgesia. There are four categories of NMDA antagonists, which are competitive antagonists, noncompetitive antagonists, uncompetitive antagonists, and glycine antagonists. Nonlimiting examples of NMDA receptor antagonists that can be used in formulations of the present invention include, but are not limited to, AP5 (APV, R-2-amino-5-phosphonopentanoate), AP7 (2-amino-7-phosphonoheptanoic acid), CPPene (3-[(R)-2-carboxypiperazin-4-yl]-prop-2-enyl-1- phosphonic acid), selfotel, amantadine, atomoxetine, AZD6765, dextrallorphan, dextromethorphan, dextrorphan, diphenidine, dizocilpine (MK-801), eticyclidine, gacyclidine, ibogaine, magnesium, memantine, methoxetamine, nitromemantine, nitrous oxide, phencyclidine, rolicyclidine, tenocyclidine, methoxydine, tiletamine, xenon, neramexanee, etoxadrol, dexoxadrol, WMS-2539, NEFA, remacemide, delucemine, 8A-PDHQ, aptiganel, HU-211, remacemide, rhynchophylline, ketamine, GLYX-13, TK-40, 1-aminocyclopropanecarboxylic acid, 7-chlorokynurenic acid, DCKA (5,7-dichlorokynurenic acid), kynurenic acid, lacosamide, and L-phenylalanine. Some synthetic opioids also function as NMDA receptor antagonists, including pethidine, methadone, dextropropoxyphene, tramadol and ketobemidone.

In other aspects of the invention, there is provided a formulation for administration to a joint fat pad of a subject, the formulation comprising a therapeutic agent selected from an analgesic agent, an anti-inflammatory agent, an immunosuppressive agent, and combinations thereof, wherein the formulation is provided as a gel solution or suspension, liposomes, a silk fibroin hydrogel, an implant, microspheres or nanospheres.

In some embodiments of the invention, the formulation is provided as a gel, for example, a gel solution or a gel suspension. The gel may be a hydrogel. The gel may contain one or more polymers. Non-limiting examples of the polymers include polysaccharides and polypeptides or proteins. In one embodiment, the polymer component is selected from the group consisting of a glycosaminoglycan (such as hyaluronic acid, also known as hyaluronan, which may be cross-linked or non-crosslinked), collagen, hyaluronic acid cross-linked with collagen, chitosan, and derivatives thereof, and combinations thereof. In a more specific embodiment, the polymer component comprises a hydrogel that undergoes sol-gel transformation via thermal, ionic, hydrophobic, pH, or catalyst induction.

Exemplary polysaccharides include, without limitation, a cellulose, an agarose, a dextran, a xylogucan, a chitosan, a chitin, a starch, a glycosaminoglycan, or derivatives thereof. A cellulose derivative includes, e.g., methylcellulose (MC) and hydroxypropyl methylcellulose (HMC). Exemplary polypeptides include, without limitation, an elastic protein (including a silk protein, a resilin, a resilin-like polypeptide (RLP), an elastin, an elastin-like polypeptide (ELP), a silk protein-elastin-like polypeptide (SELP), a gluten, an abductin, a byssus, a keratin, a gelatin, a lubricin, or a collagen. Exemplary polyesters include, without limitation, D-lactic acid, L-lactic acid, racemic lactic acid, glycolic acid, and caprolactone. Non-limiting examples of a pharmaceutically acceptable salt of a matrix polymer include sodium salts, potassium salts, magnesium salts, calcium salts, and combinations thereof.

Aspects of the present specification provide, in part, a formulation comprising a glycosaminoglycan. As used herein, the term "glycosaminoglycan" is synonymous with "mucopolysaccharide" and refers to long unbranched polysaccharides consisting of a repeating disaccharide unit. The repeating unit consists of a hexose (six-carbon sugar) or a hexuronic acid, linked to a hexosamine (six-carbon sugar containing nitrogen) and pharmaceutically acceptable salts thereof. Members of the glycosaminoglycan family vary in the type of hexosamine, hexose or hexuronic acid unit they contain, such as, e.g., glucuronic acid, iduronic acid, galactose, galactosamine, glucosamine, and may also vary in the geometry of the glycosidic linkage. Non-limiting examples of glycosaminoglycans include chondroitin sulfate, dermatan sulfate, keratan sulfate, and hyaluronan (i.e., hyaluronic acid). Non-limiting examples of acceptable salts of glycosaminoglycans include sodium salts, potassium salts, magnesium salts, calcium salts, and combinations thereof. Glycosaminoglycan and their resulting polymers useful in the methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels and Polysaccharides and Hydrogels thus Obtained, U.S. Patent Publications 2006/0194758 and 2010/0226988; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Di Napoli, Composition and Method for Intradermal Soft Tissue Augmentation, International Patent Publication WO 2004/073759.

The crosslinking of glycosaminoglycan polymers, such as hyaluronic acid, typically result in the formation of a hydrogel. Glycosaminoglycan polymers in general may be cross-linked using dialdehydes and disulfides crosslinking agents including, without limitation, multifunctional PEG-based crosslinking agents, divinyl sulfones, diglycidyl ethers, bis-epoxides, and biscarbodiimide. Non-limiting examples of glycosaminoglycan crosslinking agents include multifunctional PEG-based crosslinking agents like pentaerythritol tetraglycidyl ether (PETGE), divinyl sulfone (DVS), 1,4-butanediol diglycidyl ether (BDDE), 1,2-bis(2,3-epoxy-propoxy)ethylene (EGDGE), 1,2,7,8-diepoxyoctane (DEO), (phenylenebis-(ethyl)-carbodiimide and 1,6 hexamethylen-ebis (ethylcarbodiimide), adipic dihydrazide (ADH), bis (sulfosuccinimidyl)suberate (BS), hexamethylenediamine (HMDA), 1-(2,3-epoxypropyl)-2,3-epoxycyclohexane, or combinations thereof. Other useful cross-linking agents are disclosed in Stroumpoulis and Tezel, Tunably Crosslinked Polysaccharide Compositions, U.S. patent application Ser. No. 12/910,466, filed Oct. 22, 2010 and published as U.S. 2011/0077737, which is incorporated by reference in its entirety. Non-limiting examples of methods of crosslinking glycosaminoglycan polymers are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides, Preparation of Injectable Monophase Hydrogels, Polysaccharides and Hydrogels Obtained, U.S. Patent Publications 2006/0194758 and 2010/0226988; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Di Napoli, Composition and Method for Intradermal Soft Tissue Augmentation, International Patent Publication WO 2004/073759; Njikang et al., Dermal Filler Compositions, U.S. Patent Publication 2013/0096081; each of which is hereby incorporated by reference in its entirety.

Aspects of the present specification provide, in part, a formulation comprising a hyaluronan polymer. As used herein, the term "hyaluronan polymer" is synonymous with "hyaluronic acid polymer" and "hyaluronate polymer", and refers to an anionic, non-sulfated glycosaminoglycan polymer comprising disaccharide units, which themselves include D-glucuronic acid and D-N-acetylglucosamine monomers, linked together via alternating (β-1,4 and β-3-1,3 glycosidic bonds and pharmaceutically acceptable salts thereof. Hyaluronan polymers can be purified from animal and non-animal sources. Polymers of hyaluronan can range in size from about 5,000 Da to about 20,000,000 Da. Non-limiting examples of pharmaceutically acceptable salts of hyaluronan include sodium hyaluronan, potassium hyaluronan, magnesium hyaluronan, calcium hyaluronan, and combinations thereof. The hyaluronic acid polymer may be non-crosslinked or crosslinked. In some embodiments, a hyaluronic acid may have a molecular weight of about 200,000 daltons to about 10,000,000 daltons, about 500,000 daltons to about 10,000,000 daltons, about 1,000,000 daltons to about 5,000,000 daltons, or about 1,000,000 daltons to about 3,000,000 daltons. If the hyaluronic acid has undergone a cross-linking reaction, the resulting crosslinked macromolecular product may have a hyaluronic acid component derived from the hyaluronic acid in the crosslinking reaction. Thus, the ranges recited above may also apply to the molecular weight of a hyaluronic acid component, e.g. about 200,000 daltons to about 10,000,000 daltons, about 500,000 daltons to about 10,000,000 daltons, about 1,000,000 daltons to about 5,000,000 daltons, or about 1,000,000 daltons to about 3,000,000 daltons.

Aspects of the present specification provide, in part, a formulation comprising a chondroitin sulfate polymer. As used herein, the term "chondroitin sulfate polymer" refers to an unbranched, sulfated polymer of variable length comprising disaccharides of two alternating monosaccharides of D-glucuronic acid (GlcA) and N-acetyl-D-galactosamine (GalNAc) and pharmaceutically acceptable salts thereof. A chondroitin sulfate polymer may also include D-glucuronic acid residues that are epimerized into L-iduronic acid (IdoA), in which case the resulting disaccharide is referred to as dermatan sulfate. A chondroitin sulfate polymer can have a chain of over 100 individual sugars, each of which can be sulfated in variable positions and quantities. Chondroitin sulfate polymers are an important structural component of cartilage and provide much of its resistance to compression. Non-limiting examples of pharmaceutically acceptable salts of chondroitin sulfate include sodium chondroitin sulfate, potassium chondroitin sulfate, magnesium chondroitin sulfate, calcium chondroitin sulfate, and combinations thereof.

Aspects of the present specification provide, in part, a formulation comprising a keratan sulfate polymer. As used herein, the term "keratan sulfate polymer" refers to a polymer of variable length comprising disaccharide units, which themselves include β-D-galactose and N-acetyl-D-galactosamine (GalNAc) and pharmaceutically acceptable salts thereof. Disaccharides within the repeating region of keratan sulfate may be fucosylated and N-acetylneuraminic acid caps the end of the chains. Non-limiting examples of pharmaceutically acceptable salts of keratan sulfate include sodium keratan sulfate, potassium keratan sulfate, magnesium keratan sulfate, calcium keratan sulfate, and combinations thereof.

Aspects of the present specification provide, in part, a formulation comprising an elastic protein. As used herein, the term "elastic protein" is synonymous with "bioelastomer" and refers to a polypeptide possessing rubber-like elasticity. An elastic protein can undergo high deformation without rupture, storing the energy involved in deformation and then returning to its original state when the stress is removed. The latter phase is passive and returns all, or nearly all, of the energy used in deformation. As such, an elastic protein has high resilience in that the polypeptide can be deformed reversibly without little loss of energy. Additionally, an elastic protein can be deformed to large strains with little force, and/or has low stiffness in that the polypeptide can be stretched. In general, properties useful to characterize elastic protein include stiffness, as evaluated by the modulus of elasticity ($E_{init}$, Nm-2); strength, as evaluated by the stress at fracture ($\sigma_{max}$, Nm-2); toughness, as evaluated by the energy to break work of fracture (Jm-3, Jm-2); extensibility, as evaluated by the strain at fracture ($\varepsilon_{max}$, no units); spring efficiency, as evaluated by resilience (%); durability, as evaluated by lifetime fatigue (s to failure or cycles of failure); and spring capacity, as evaluated by energy storage capacity ($W_{out}$, Jkg-1). For example, elastic proteins like elastin and resilin have a combination of high resilience, large strains and low stiffness is characteristic of rubber-like proteins that function in the storage of elastic-strain energy. Other elastic proteins, like collagens, provide exceptional energy storage capacity but are not very stretchy. Mussel byssus threads and spider dragline silks are also elastic proteins because they are remarkably stretchy, in spite of their considerable strength, low resilience, and stiffness.

Non-limiting examples of elastic proteins include silk proteins, resilins, resilin-like polypeptides (RLPs), elastins (including tropoelastin, fibrillin and fibullin), elastin-like polypeptides (ELPs), glutens (including gliadins and glutenins), abductins, byssuss, and collagens. In general, elastic proteins have at least one domain containing elastic repeat motifs and another non-elastic domain where crosslinks can be formed. See, e.g., Tatham and Shewry, Comparative Structures and Properties of Elastic Proteins, *Phil. Trans. R. Soc. Lond. B* 357: 229-234 (2002), which is hereby incorporated by reference in its entirety. However, both resilin and abductin are exceptions since crosslinking can occur within the elastic repeat motif.

Collagen is a protein that forms fibrils and sheets that bear tensile loads. Collagen also has specific integrin-binding sites for cell adhesion and is known to promote cell attachment, migration, and proliferation. The collagen superfamily contains at least 29 different types of collagen, designated COL1A1-COL29A1. Some collagens have several isoforms, such as, e.g., COL1A1, COL1A2, COL4A1, COL4A2, COL4A3, COL4A4, COL4A5, COL4A6, COL5A1, COL5A2, COL5A3, COL6A1, COL6A2, COL6A3, COL8A1, COL8A2, COL9A1, COL9A2, COL9A3, COL11A1, and COL11A2. Collagens are found in all connective tissue and are a major component of the extracellular matrix. Collagens can be purified from animal sources, plant sources, or produced recombinantly. Although 29 types of collagen have been identified, over 90% of the collagen in the body is of type I, II, III, and IV. Collagen may be positively charged because of its high content of basic amino acid residues such as arginine, lysine, and hydroxylysine. Unless clearly indicated otherwise, reference to collagen herein may include uncharged collagen, as well as any cationic forms, anionic forms, or salts of collagen.

Other elastic proteins useful in the compositions and methods disclosed herein are described in, e.g., Masters, Protein Matrix Materials, Devices and Methods of Making and Using Thereof, U.S. Pat. No. 7,662,409; and Kaplan, et al., Fibrous Protein Fusions and Use Thereof in the Formation of Advanced Organic/Inorganic Composite Materials, U.S. Patent Publication 2008/0293919.

Aspects of the present specification provide, in part, a formulation comprising a viscoelastic hydrogel. As used herein, the term "viscoelastic hydrogel" refers to a hydrated polymer composed of one or more components and possessing both viscous and elastic characteristics. As such, a viscoelastic hydrogel can behave similar to an elastic protein (i.e. can be deformed reversibly with little loss of energy), similar to a viscous fluid (i.e. the stress is dependent on the strain rate and the energy dissipates over time), or as a combination of an elastic protein and a viscous fluid. Rheologic analysis, in which oscillatory stresses are applied and the resulting strain is measured is used to characterize viscoelastic materials. In general, properties useful to characterize viscoelastic materials include measures related to elasticity, as evaluated by the shear storage modulus ($G'$, $Nm^{-2}$); related to viscosity, as evaluated by the loss modulus ($G''$, $Nm^{-2}$); and phase lag of strain with respect to stress, as evaluated by the phase angle ($\tan \delta = G''/G'$). For example, viscoelastic materials like hydrogels and cartilage have an elastic component that function in the storage of elastic-strain energy and a viscous component that dissipates energy over time.

A formulation disclosed herein can include a single polymer or a plurality of polymers. In aspects of this embodiment, a formulation may comprise, e.g., two polymers, three polymers, four polymers, five polymers, or six polymers. In other aspects of this embodiment, a three-dimensional matrix may comprise, e.g., at least two polymers, at least three polymers, at least four polymers, at least five polymers, or at least six polymers. In yet other aspects of this embodiment, a three-dimensional matrix may comprise from between, e.g., one and two polymers, one and three polymers, one and four polymers, one and five polymers, one and six polymers, two and three polymers, two and four polymers, two and five polymers, two and six polymers, three and four polymers, three and five polymers, or three and six polymers. Whether present in the three-dimensional matrix as a single polymer or a plurality of polymers, the polymers may be synthetically linked to one another.

In one embodiment, the polymer component is a hyaluronic acid cross-linked to a collagen. For a three-dimensional matrix comprising a hyaluronic acid cross-linked to a collagen, any suitable weight ratio of the hyaluronic acid component to the collagen component may be used. For example, a crosslinked macromolecular matrix may have a weight ratio of hyaluronic acid:collagen of about 1:2 to about 10:1, about 1:1 to about 7:1, about 2:1 to about 3:1, about 1:1 to about 3:1, about 1:1 to about 2:1, about 1:1, about 2:1, about 3:1, about 7:2, about 4:1, about 5:1, about 16:3, about 6:1, about 7:1, or any weight ratio in a range bounded by, and/or between, any of these values. In some embodiments, the weight ratio of hyaluronic acid to collagen in a crosslinked matrix may be about 12 mg/mL of hyaluronic acid to about 6 mg/mL collagen, about 12 mg/mL of hyaluronic acid to about 12 mg/mL collagen, or about 16 mg/mL of hyaluronic acid to about 8 mg/mL collagen. In some embodiments, the collagen may be type I collagen.

In some embodiments, the therapeutic agent is directly incorporated into the gel to provide a gel solution or a gel suspension.

In some embodiments, the therapeutic agent is incorporated into a biocompatible or biodegradable vessel. Such vessels can be composed of non-covalently or covalently linked self-assembled molecules such as liposomes, micelles, and polymerized vesicles. The therapeutic agent may be encapsulated into the vessels (i.e., the liposomes, micelles, and/or polymerized vescicles) to enable local (injection site), sustained and controlled release of the therapeutic agent. This method provides a composition that persists by allowing the agent to avoid the natural degradation mechanisms encountered in vivo. A liposome is a vesicle composed of one or more bilayer membranes formed of naturally-derived phospholipids with mixed lipid chains (such as egg phosphatidylethanolamine), or of pure surfactant components like dioleoylphosphatidylethanolamine (DOPE). Liposomes, usually but not by definition, contain a core of aqueous solution; lipid structures that contain no aqueous material are called micelles. A micelle is an aggregate of surfactant molecules dispersed in a liquid colloid. A typical micelle in aqueous solution forms an aliphatic aggregate with the hydrophilic "head" regions in contact with surrounding solvent, sequestering the hydrophobic"tail" regions in the micelle center. This type of micelle is known as a normal phase micelle (oil-in-water micelle). Inverse micelles have the head groups at the center with the tails extending out (water-in-oil micelle). Micelles are often approximately spherical in shape, however, other forms, including shapes such as ellipsoids, cylinders, and bilayers are also possible. The shape and size of a micelle is a function of the molecular geometry of its surfactant molecules and solution conditions such as surfactant concentration, temperature, pH, and ionic strength. The process of forming micelles is known as micellisation and forms part of the phase behavior of many lipids according to their polymorphism.

In some embodiments, a vessel comprising a therapeutic agent is further incorporated into a gel composition. In one such embodiment, a liposomal vessel comprising a therapeutic agent is incorporated into a gel composition, such as a hydrogel; the hydrogel may comprise hyaluronic acid, which may be cross-linked.

In some embodiments of the invention, the formulation is provided as a silk fibroin hydrogel. Silk fibroin hydrogel compositions as drug delivery platforms, including sustained release drug delivery platforms, have been described, for example, in US 2011/0111031 A1 and US 2011/0052695 A1, the entire contents of each of which is incorporated in its entirety herein by this specific reference.

In some embodiments of the invention, the formulation is provided as an implant. The implants are structured and/or configured to be placed in a joint fat pad of a subject. Certain implants can be administered to a joint fat pad and provide therapeutic benefits for prolonged periods of time without being compromised by movements of the joint bones.

The implants may be monolithic implants, i.e., having the therapeutically active agent or agents homogenously distributed through the polymeric matrix, or encapsulated, where a reservoir of active agent is encapsulated by the polymeric matrix. Due to ease of manufacture, monolithic implants may be preferred over encapsulated forms. However, the greater control afforded by the encapsulated, reservoir-type implant may be of benefit in some circumstances, where the therapeutic level of the drug falls within a narrow window. In addition, the therapeutic component may be distributed in a non-homogenous pattern in the matrix. For example, the implant may include a portion that has a greater concentration of the therapeutic agent relative to a second portion of the implant.

The implants may be of any geometry including fibers, sheets, films, spheres, circular discs, plaques and the like. The upper limit for the implant size will be determined by factors such as toleration for the implant, size limitations on insertion, ease of handling, etc.

In other embodiments of the invention, the formulation is provided as microspheres or nanospheres. In further embodiments of the invention, drug particles or drug-containing microspheres or nanospheres are suspended in a crosslinked hydrogel.

Suitable polymeric materials or compositions for use in the implant, microspheres or nanospheres include those materials which are compatible, that is, biocompatible, with the joint fat pad and surrounding tissues so as to cause no substantial interference with the functioning or physiology of the joint. Included among polymers of interest are polyesters, for example, homo- or copolymers of aliphatic polyesters like D-lactide, L-lactide, poly(D,L-lactide), or racemic lactide polymers, collectively referred to as PLA polymers; D-glycolide, L-glycolide, or racemic glycolide polymers, collectively referred to as PGA polymers; poly (D,L-lactide-co-glycolide) or poly(L-lactide-co-glycolide) copolymers, collectively referred to as PLGA copolymers; poly(caprolactone) (PCL) polymers, such as poly(ε-caprolactone).

Also of interest are a polyether, poly(dioxanone), poly (ethylene glycol), poly(ortho-ester), polyphosphazine, polyanhydride, poly(propylene oxide), poly(propylene fumarate), poly(phosphate ester), polyvinyl alcohol, silicone, natural polymers such as latex, polysaccharides, proteins such as gelatin or collagen, or polymeric blends; and combinations of the foregoing. Among the useful polysaccharides are, without limitation, calcium alginate, and functionalized celluloses, particularly carboxymethylcellulose esters characterized by being water insoluble. Of additional interest are polymers of hydroxyaliphatic carboxylic acids, either homopolymers or copolymers.

In some embodiments, the polymeric materials are at least partially and more preferably substantially completely biodegradable or bioerodible. Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. nonoxocarbonyl, such as carboxylic acid ester, and the like. The nitrogen may be present as amide, cyano and amino. The polymers set forth in Heller, Biodegradable Polymers in Controlled Drug Delivery, In: *CRC Critical Reviews in Therapeutic Drug Carrier Systems*, Vol. 1, CRC Press, Boca Raton, Fla. 1987, pp 39-90, which describes encapsulation for controlled drug delivery, may find use in the present implants.

The biodegradable polymeric materials which are included to form the polymeric matrix are desirably subject to enzymatic or hydrolytic instability. The degree of stability can be varied widely, depending upon the choice of monomer, whether a homopolymer or copolymer is employed, employing mixtures of polymers, and whether the polymer includes terminal acid groups. The biodegradable polymer matrix may comprise a mixture of two or more biodegradable polymers. For example, matrix may comprise a mixture of a first biodegradable polymer and a different second biodegradable polymer. One or more of the biodegradable polymers may have terminal acid groups.

When copolymers of glycolic acid and lactic acid are used, the rate of biodegradation may be controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The percentage of polylactic acid in the PLGA copolymer can be 0-100%, preferably about 15-85%, more preferably about 35-65%. In some matrices, a 50/50 PLGA copolymer is used.

Equally important to controlling the biodegradation of the polymer and hence the sustained release profile of the therapeutic agent is the relative average molecular weight of the polymeric composition employed in the matrix. Different molecular weights of the same or different polymeric compositions may be included in the matrix to modulate the release profile. For example, in certain implants, the relative average molecular weight of the polymer will range from about 9 to about 64 kD, usually from about 10 to about 54 kD, and more usually from about 12 to about 45 kD.

Release of a drug from an erodible polymer is the consequence of several mechanisms or combinations of mechanisms. Some of these mechanisms include desorption from the surface of the polymer matrix; dissolution; diffusion through porous channels of the hydrated polymer; and erosion. Erosion can be bulk erosion, or surface erosion, or a combination of both. The sustained release formulation may release drug at a rate effective to sustain release of an amount of the therapeutic agent for one week or more after implantation into a fat pad. In certain sustained release formulations, effective amounts of the therapeutic agent are released for at least one week, at least two weeks, or at least three weeks. For example, the matrix may degrade at a rate effective to sustain release of an effective amount of the therapeutic agent for more than 30 or 40 days, such as for about six months, about 12 months, about 18 months, or about 24 months.

The release of the therapeutic agent from the formulation comprising a biodegradable polymer matrix may include an initial burst of release followed by a gradual increase in the amount of the therapeutic agent released, or the release may include an initial delay in release of the therapeutic agent followed by an increase in release. When the formulation is substantially completely degraded, the percent of the therapeutic agent that has been released is about one hundred.

Formulations of the present invention can further comprise degradation inhibitors. Degradation inhibitors, include but are not limited to, glycosaminoglycans (e.g., heparin, heparin sulfate, dermatan sulfate, chrondroitin sulfate, o-sulfated hyaluronic acid, inamarin, and amygdalin), antioxidants (e.g. ascorbic acid, melatonin, vitamin C or a vitamin E such as D-alpha-tocopheryl polyethylene glycol 1000 succinate (TPGS)), proteins (e.g., serum hyaluronidase inhibitor), and fatty acids (e.g. saturated $C_{10}$ to $C_{22}$ fatty acids).

Pharmaceutically acceptable excipients for use with the invention include but are not limited to preservatives, buffering agents, antioxidants, lipophilic vehicles, hydrophilic vehicles, tonicity agents, electrolytes, thickeners, neutralizing agents, emulsifiers, dispersing agents, demulcents, plasticizers, occlusive agents, and film formers, and combinations thereof. Certain compositions may include excipients to adjust the hydrophobicity of the formulation, for example, poly(ethylene glycol), short chain fatty acids, waxes, co-solvents, or other compounds.

Effective amounts of the therapeutic agent and therapeutic doses may be determined by one of ordinary skill in the art but will vary depending on the therapeutic agent employed, the mode of administration, the frequency of administration, the release rate from the formulation, and the physical and chemical composition of the formulation. The actual dose of the therapeutic agent to be administered in any given case will be determined by a physician taking into account the relevant circumstances, such as the condition to be treated, the severity of the condition, the age and weight of the patient, the patient's general physical condition, the cause of the condition, and the desired result.

The amount of therapeutic agent in the sustained release formulation will generally range from about 0.0001% to about 70% by weight of the composition, from about 0.01% to about 70%, by weight of total composition, preferably from about 0.1% to about 50% by weight of the composition. In certain embodiments, the therapeutic agent is about 2% by weight, about 10% by weight, or about 20% by weight of the composition.

The formulations of the present invention may release the therapeutic agent at a rate effective to sustain release of an amount of the therapeutic agent for one week or more after implantation into a fat pad. In some embodiments, effective amounts of the therapeutic agent are released for at least about one week, at least about two weeks, at least about three weeks, at least about four weeks, at least about a month, or at least about 30 to 35 days after administration. In some embodiments, effective amounts of the therapeutic agent are released for more than about 30-35 days after administration. In some embodiments, effective amounts of the therapeutic agent are released for up to about six months, about 12 months, about 18 months, or about 24 months. In some embodiments, the sustained release occurs over a period of up to about 6 to 24 months, about 6 to 18 months, about 6 to 12 months, or about 12 to 18 months.

Additionally, the formulations may be designed to delay release of the compound over a given period of time, or to carefully control the amount of compound released at a given time during the course of treatment.

The formulation compositions may be administered at a frequency and for a period of time necessary to achieve the desired results. The administration can be on a monthly or bi-monthly basis. The administration can be once every 1, 2, 3, 4, 5 or 6 months. The administration can be once every 6, 12, 18 or 24 months. In certain embodiments, the compositions can be administered on an ongoing basis to maintain a desired result.

In some aspects, the method of treating the subject comprising administering a sustained release formulation described herein to a fat pad of a joint of a subject relieves the joint from pain, inflammation, or disease for a period of at least about one week, about two weeks, about three weeks, about four weeks, about one month, about two months, about three months, about four months, about five months or about six months after administering the formulation to the joint fat pad. In further aspects, the method relieves the joint from pain, inflammation, or disease for a period of up to about six months, about 12 months, about 18 months, or about 24 months.

Aspects of the present specification provide, in part, administering a formulation composition disclosed herein. The actual delivery mechanism used to administer a composition to an individual can be determined by a person of ordinary skill in the art by taking into account factors, including, without limitation, the type of condition, the location of the condition, the cause of the condition, the severity of the condition, the degree of relief desired, the duration of relief desired, the particular composition used, the rate of excretion of the particular composition used, the pharmacodynamics of the particular composition used, the nature of the other compounds included in the particular composition used, the particular route of administration, the particular characteristics, history and risk factors of the individual, such as, e.g., age, weight, general health and the like, or any combination thereof.

The following are non-limiting embodiments of the invention. It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Each and every feature described herein, and each and every combination of two or more of such features, is included within the scope of the present invention provided that the features included in such a combination are not mutually inconsistent.

In the following listing of embodiments, cross-reference to another "parent" embodiment includes reference to all of its narrower and dependent "child" embodiments. For example, reference to a formulation for use according to embodiment (121) includes parent embodiment (121) and each of its child embodiments (121a) through (121h).

In embodiment (1), there is provided a formulation for administration to a joint fat pad of a subject, the formulation comprising:

a therapeutic agent selected from an analgesic agent, an anti-inflammatory agent, an immunosuppressive agent, and combinations thereof;

wherein the formulation provides sustained release of the therapeutic agent to the joint.

In embodiment (2), there is provided a formulation of embodiment (1), wherein the formulation provides a therapeutically effective amount of the therapeutic agent, thereby relieving the joint from pain, inflammation or disease.

In embodiment (3), there is provided a formulation of embodiment (1) or (2), wherein the joint is an arthritic joint, an injured joint or a surgically replaced joint.

In embodiment (4), there is provided a formulation of any one of embodiments (1), (2) or (3), wherein the joint is a synovial joint.

In embodiment (5), there is provided a formulation of any one of embodiments (1) through (4), wherein the joint is a knee joint, and the fat pad is an infrapatellar fat pad, a suprapatellar fat pad, or an anterior femoral fat pad.

In embodiment (6), there is provided the formulation of any one of embodiments (1) through (5), wherein the therapeutic agent is an anti-inflammatory agent selected from the group consisting of steroidal anti-inflammatory agents, non-steroidal anti-inflammatory agents (NSAIDs), anti-inflammatory cytokines, antimetabolites, N-Methyl-D-aspartate (NMDA) receptor antagonists, and combinations thereof.

In embodiment (7), there is provided the formulation of any one of embodiments (1) through (6), wherein the therapeutic is a steroidal anti-inflammatory agent selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, fluocinonide, fluocinolone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol, mazipredone, medrysone, meprednisone, methylprednisolone, mometasone furoate, paramethasone, paramethasone acetate, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, derivatives of the foregoing, and combinations thereof.

In embodiment (8), there is provided the formulation of any one of embodiments (1) through (5), wherein the therapeutic agent is an immunosuppressive agent selected from the group consisting of azathioprine, cyclosporine (such as cyclosporine A), mizoribine, tacrolimus, derivatives of the foregoing, and combinations thereof.

In embodiment (9), there is provided the formulation of any one of embodiments (1) through (5), wherein the therapeutic agent is an analgesic selected from acetaminophen (paracetamol), opiates, non-steroidal anti-inflammatory agents (NSAIDS), steroidal anti-inflammatory agents, cyclooxygenase-2 (COX2) inhibitors, N-Methyl-D-aspartate receptor (NMDA) receptor antagonists, derivatives of the foregoing, and combinations thereof.

In embodiment (10), there is provided the formulation of any one of embodiments (1) through (9), wherein the formulation is provided as a gel, an implant, a silk fibroin hydrogel, microspheres, nanospheres or liposomes.

In embodiment (11), there is provided the formulation of any one of embodiments (1) through (10), wherein the formulation is provided as microspheres, nanospheres, or an implant, which is optionally a solid implant, wherein the microspheres, nanospheres or implant comprises a polymer, optionally a biodegradable polymer; in some aspects, the polymer is selected from the group consisting of poly(D,L-lactide-co-glycolide), poly (D,L-lactide), poly(ethylene glycol), poly(propylene fumarate), poly(vinyl alcohol), poly (dioxanone), poly(caprolactone), poly(propylene fumarate), poly(propylene oxide), polyanhydrides, polyphosphazenes, polysaccharides, proteins, and combinations thereof.

In embodiment (12), there is provided the formulation of embodiment (11), wherein the polysaccharide is selected from agarose, alginate (such as calcium alginate), chitosan, carboxymethylcellulose, hyaluronic acid and combinations thereof.

In embodiment (13), there is provided the formulation of embodiment (11), wherein the protein is collagen, gelatin, fibrin, or a combination thereof.

In embodiment (14), there is provided the formulation of any one of embodiments (1) through (10), wherein the formulation is provided as a gel solution or gel suspension, wherein the gel is optionally a hydrogel.

In embodiment (15), there is provided the formulation of embodiment (14), wherein the gel comprises a polysaccharide, a protein or a combination thereof.

In embodiment (16), there is provided the formulation of embodiment (15), wherein the polysaccharide is hyaluronic acid, which may be crosslinked or noncrosslinked.

In embodiment (17), there is provided the formulation of embodiment (15), wherein the protein is selected from collagen, gelatin, fibrin, and a combination thereof.

In embodiment (18), there is provided the formulation of embodiment (15), where the hydrogel comprises a polysaccharide crosslinked to a protein.

In embodiment (19), there is provide the formulation of embodiment (18), wherein the polysaccharide is hyaluronic acid and the protein is collagen.

In embodiment (20), there is provided the formulation of any one of embodiments (1) through (19), wherein the sustained release occurs over a period of (a) at least about one week, about two weeks, about three weeks, about four weeks, about one month, about two months, about three months, about four months, about five months after administering the formulation to the fat pad; or (b) up to about 6 months, up to about 12 months, about 18 months, or about 24 months after administering the formulation to the joint fat pad; or (c) any period of time specified in (a) or (b), for example, at least about 6 months; or (d) any combination of each period of time specified in (a) and (b), for example, for at least about one month and up to about 18 months.

In embodiment (21), there is provided the formulation of any one of embodiments (1) through (20), wherein the sustained release occurs over a period of up to about 6 to about 24 months, about 6 to about 18 months, about 6 to about 12 months, about 12 to about 24 months, about 12 to about 18 months, or at least about 12 months.

In embodiment (22), there is provided the formulation of any one of embodiments (1) through (21), the formulation providing at least one of reduced systemic exposure, reduced side effects, enhanced dosing precision, and reduced frequency of administration, wherein each reduction or enhancement is relative to a systemic or an intra-articular administration of a therapeutic dose, such as a routine therapeutic dose, of the therapeutic agent.

In embodiment (23), there is provided the formulation of any one of embodiments (2) through (22), wherein a single administration of the formulation to the joint fat pad provides equivalent or superior relief of the pain, inflammation or disease of the joint relative to a single systemic or intra-articular administration of a therapeutic dose, such as a routine therapeutic dose, of the therapeutic agent.

In embodiment (24), there is provided a method of treating pain, inflammation, or disease in a joint of a subject, the method comprising administering a formulation of any one of embodiments (1) through (23) to a fat pad of the joint.

In embodiment (25), there is provided the method of embodiment (24), wherein the method provides a therapeutically effective amount of the therapeutic agent, thereby relieving the joint from the pain, inflammation or disease.

In embodiment (26), there is provided the method of embodiment (24) or (25), wherein the joint is an arthritic joint, an injured joint or a surgically replaced joint.

In embodiment (27), there is provided the method of any one of embodiments (24) through (26), wherein the joint is a synovial joint.

In embodiment (28), there is provided the method of any one of embodiments (24) through (27), wherein the joint is a knee joint, and the fat pad is an infrapatellar fat pad, a suprapatellar fat pad, or an anterior femoral fat pad of the knee joint.

In embodiment (29), there is provided the method of any one of embodiments (24) through (28), wherein the administering comprises injecting, embedding or implanting the formulation into the fat pad.

In embodiment (30), there is provided the method of any one of embodiments (24) through (29), wherein the pain, inflammation or disease is associated with osteoarthritis, rheumatoid arthritis, juvenile arthritis, calcium pyrophosphate dehydrate crystal deposition disease (CPPD, or pseudo gout), post-operative pain, joint replacement surgery pain or a combination thereof.

In embodiment (31), there is provided the method of any one of embodiments (24) through (30), wherein the method relieves the joint from the pain, inflammation, or disease for a period of (a) at least about one week, about two weeks, about three weeks, about four weeks, about one month, about two months, about three months, about four months, about five months after administering the formulation to the fat pad; or (b) up to about 6 months, up to about 12 months, about 18 months, or about 24 months after administering the formulation to the joint fat pad; or (c) any period of time specified in (a) or (b), for example, at least about 6 months; or (d) any combination of each period of time specified in (a) and (b), for example, for at least about one month and up to about 18 months.

In embodiment (32), there is provided the method of any one of embodiments (24) through (31), the method providing at least one of reduced systemic exposure, reduced side effects, enhanced dosing precision, and reduced frequency of administration; wherein each reduction or enhancement is relative to a systemic or intra-articular administration of a therapeutic dose, such as a routine therapeutic dose, of the therapeutic agent.

In embodiment (33), there is provided the method of any one of embodiments (24) through (32), wherein the treating comprises one or more administrations of the formulation to the joint fat pad.

In embodiment (34), there is provided the method of any one of embodiments (24) through (33), wherein the treating comprises a single administration of the formulation to the joint fat pad.

In embodiment (35), there is provided the method of embodiment (34), wherein the single administration provides a therapeutically effective amount of the therapeutic agent to the joint, thereby relieving the joint from the pain, inflammation or disease.

In embodiment (36), there is provided the method of embodiment (34) or (35), wherein the single administration of the formulation to the joint fat pad relieves the joint from the pain, inflammation, or disease for a period of (a) at least about one week, about two weeks, about three weeks, about four weeks, about one month, about two months, about three months, about four months, about five months after administering the formulation to the fat pad; or (b) up to about 6 months, up to about 12 months, about 18 months, or about 24 months after administering the formulation to the joint fat pad; or (c) any period of time specified in (a) or (b), for example, at least about 6 months; or (d) any combination of each period of time specified in (a) and (b), for example, for at least about one month and up to about 18 months.

In embodiment (37), there is provided the method of any one of embodiments (34) through (36), wherein the single administration of the formulation to the joint fat pad delivers the therapeutically effective amount of the therapeutic agent with reduced systemic exposure or reduced side effects relative to a single systemic or a single intra-articular administration of a therapeutic dose, such as a routine therapeutic dose, of the therapeutic agent.

In embodiment (38), there is provided the method of any one of embodiments (34) through (37), wherein the single administration of the formulation to the joint fat pad provides equivalent or superior relief of the pain, inflammation or disease of the joint relative to a single systemic or intra-articular administration of a therapeutic dose, such as a routine therapeutic dose, of the therapeutic agent.

In embodiment (39), there is provided a formulation of any one of embodiments (1)-(7), (9)-(10), (14)-(16) and (20)-(23), wherein the therapeutic agent is dexamethasone, and the formulation is provided as a gel.

In embodiment (40), there is provided a gel formulation of embodiment (39), wherein the formulation is provided as a gel suspension.

In embodiment (41), there is provided a gel formulation of embodiment (39) or (40), wherein the gel comprises hyaluronic acid.

In embodiment (42), there is provided a gel formulation of any one of embodiments (39) through (41), wherein the dexamethasone is provided at a concentration ranging from about 0.1% to about 50% (wt/wt), about 0.5% to about 30% (wt/wt), about 1% to about 25% (wt/wt), or about 2% to about 20% (wt/wt) of the formulation.

In embodiment (43), there is provided a gel formulation of any one of embodiments (39) through (42), wherein the dexamethasone is provided at a concentration of about 2%, about 10% or about 20% (wt/wt) of the formulation.

In embodiment (44), there is provided a gel formulation of any one of embodiments (39) through (43), wherein the dexamethasone concentration is about 2%, about 10% or about 20% (wt/wt), of the formulation.

In embodiment (45), there is provided a gel formulation of any one of embodiments (41) through (44), wherein the hyaluronic acid concentration is about 1% to about 10% (wt/wt), or about 1% to about 5% (wt/wt), or about 2% (wt/wt), of the formulation.

In embodiment (45), there is provided a gel formulation of any one of embodiments (39) through (44), wherein the formulation provides a therapeutically effective concentration of dexamethasone for up to about six months, up to about 12 months, up to about 18 months, or up to about 24 months.

In embodiment (46), there is provided a gel formulation of any one of embodiments (39) through (45), wherein the sustained release occurs over a period of (a) at least about one week, about two weeks, about three weeks, about four weeks, about one month, about two months, about three months, about four months, about five months after administering the formulation to the fat pad; or (b) up to about 6 months, up to about 12 months, about 18 months, or about 24 months after administering the formulation to the joint fat pad; or (c) any period of time specified in (a) or (b), for example, at least about 6 months; or (d) any combination of each period of time specified in (a) and (b), for example, for at least about one month and up to about 18 months.

In embodiment (47), there is provided a formulation of any one of embodiments (39) through (46), wherein the formulation provides at least one of reduced systemic exposure, reduced side effects, enhanced dosing precision, and reduced frequency of administration, wherein each reduction or enhancement is relative to a systemic or an intra-articular administration of a therapeutic dose, such as a routine therapeutic dose, of dexamethasone.

In embodiment (48), there is provided the formulation of any one of embodiments (39) through (47), wherein a single administration of the formulation to the joint fat pad provides equivalent or superior relief of the pain, inflammation or disease of the joint relative to a single systemic or intra-articular administration of a therapeutic dose, such as a routine therapeutic dose, of dexamethasone.

In embodiment (49), there is provided the formulation of any one of embodiments (39) through (48), wherein a single administration of the formulation to the joint fat pad provides reduced systemic exposure and equivalent or superior relief of the pain, inflammation or disease of the joint relative to a single systemic or intra-articular administration of a therapeutic dose, such as a routine therapeutic dose, of dexamethasone.

In embodiment (50), there is provided the method of treating pain, inflammation, or disease in a joint of a subject, the method comprising administering a formulation of any one of embodiments (39)-(49) to a fat pad of the joint.

In embodiment (51), there is provided the method of embodiment (50), wherein the method provides a therapeutically effective amount of the dexamethasone, thereby relieving the joint from pain, inflammation or disease.

In embodiment (52), there is provided the method of embodiment (50) or (51), wherein the joint is an arthritic joint, an injured joint or a surgically replaced joint.

In embodiment (53), there is provided the method of any one of embodiments (50) through (52), wherein the joint is a synovial joint.

In embodiment (54), there is provided the method of any one of embodiments (50) through (53), wherein the joint is a knee joint, and the fat pad is an infrapatellar fat pad, a suprapatellar fat pad, or an anterior femoral fat pad of the knee joint.

In embodiment (55), there is provided the method of any one of embodiments (50) through (54), wherein the administering comprises injecting, embedding or implanting the gel formulation into the fat pad.

In embodiment (56), there is provided the method of any one of embodiments (50) through (55), wherein the pain, inflammation or disease is associated with osteoarthritis, rheumatoid arthritis, juvenile arthritis, calcium pyrophosphate dehydrate crystal deposition disease (CPPD, or pseudo gout), post-operative pain, joint replacement surgery pain or a combination thereof.

In embodiment (57), there is provided the method of any one of embodiments (50) through (56), wherein the method relieves the joint from the pain, inflammation, or disease for a period of (a) at least about one week, about two weeks, about three weeks, about four weeks, about one month, about two months, about three months, about four months, about five months after administering the formulation to the fat pad; or (b) up to about 6 months, up to about 12 months, about 18 months, or about 24 months after administering the formulation to the joint fat pad; or (c) any period of time specified in (a) or (b), for example, at least about 6 months; or (d) any combination of each period of time specified in (a) and (b), for example, for at least about one month and up to about 18 months.

In embodiment (58), there is provided the method of any one of embodiments (50) through (57), the method providing at least one of reduced systemic exposure, reduced side effects, enhanced dosing precision, and reduced frequency of administration; wherein each reduction or enhancement is relative to a systemic or intra-articular administration of a therapeutic dose, such as a routine therapeutic dose, of the dexamethasone.

In embodiment (59), there is provided the method of any one of embodiments (50) through (58), wherein the treating comprises one or more administrations of the gel formulation to the joint fat pad.

In embodiment (60), there is provided the method of any one of embodiments (50) through (59), wherein the treating comprises a single administration of the gel formulation to the joint fat pad.

In embodiment (61), there is provided the method of embodiment (60), wherein the single administration provides a therapeutically effective amount of the dexamethasone to the joint, thereby relieving the joint from the pain, inflammation or disease.

In embodiment (62), there is provided the method of embodiment (60) or (61), wherein the single administration of the gel formulation to the joint fat pad relieves the joint from the pain, inflammation, or disease for a period of (a) at least about one week, about two weeks, about three weeks, about four weeks, about one month, about two months, about three months, about four months, about five months after administering the formulation to the fat pad; or (b) up to about 6 months, up to about 12 months, about 18 months, or about 24 months after administering the formulation to the joint fat pad; or (c) any period of time specified in (a) or (b), for example, at least about 6 months; or (d) any combination of each period of time specified in (a) and (b), for example, for at least about one month and up to about 18 months.

In embodiment (63), there is provided the method of any one of embodiments (60) through (62), wherein the single administration of the gel formulation to the joint fat pad delivers the therapeutically effective amount of the dexamethasone with reduced systemic exposure or reduced side effects relative to a single systemic or a single intra-articular administration of a therapeutic dose, such as a routine therapeutic dose, of dexamethasone.

In embodiment (64), there is provided the method of any one of embodiments (60) through (63), wherein the single administration of the gel formulation to the joint fat pad provides equivalent or superior relief of the pain, inflammation or disease of the joint relative to a single systemic or intra-articular administration of a therapeutic dose, such as a routine therapeutic dose, of dexamethasone.

In embodiment (65), there is provided the method of any one of embodiments (60) through (64), wherein a single administration of the gel formulation to the joint fat pad provides reduced systemic exposure and equivalent or superior relief of the pain, inflammation or disease of the joint relative to a single systemic or intra-articular administration of a therapeutic dose, such as a routine therapeutic dose, of dexamethasone.

In embodiment (66), there is provided the formulation of any one of embodiments (39)-(49), wherein the gel comprises hyaluronic acid and water or a buffering agent.

In embodiment (67), there is provided the formulation of embodiment (66), wherein the the gel comprises hyaluronic acid and phosphate buffered saline.

In embodiment (68), there is provided the formulation of any one of embodiments (1) through (7) and (9) through (11), wherein the therapeutic agent is dexamethasone, and the formulation is provided as an implant.

In embodiment (69), there is provided the formulation of embodiment (68), wherein the implant comprises a polymer selected from the group consisting of poly(D,L-lactide-co-glycolide), poly (D,L-lactide), poly(ethylene glycol), poly (propylene fumarate), poly(vinyl alcohol), poly(dioxanone), poly(caprolactone), poly(propylene fumarate), poly(propylene oxide), polyanhydrides, polyphosphazenes, polysaccharides, proteins, and combinations thereof.

In embodiment (70), there is provided the formulation of embodiment (68) or (69), wherein the implant comprises a polymer selected from poly(D,L-lactide-co-glycolide), poly(D,L-lactide), and combinations thereof; in further embodiment (70a), the polymer is poly(D,L-lactide-co-glycolide).

In embodiment (71), there is provided the formulation of any one of embodiments (68) through (70), wherein the dexamethasone represents from about 0.1% to about 70% (wt/wt), about 0.1% to about 60% (wt/wt), about 0.5% to about 50% (wt/wt), about 1% to about 30% (wt/wt), about 1% to about 25% (wt/wt), about 1% to about 20% (wt/wt), about 2% to about 70% (wt/wt), about 5% to about 70% (wt/wt), about 5% to about 60% (wt/wt), or about 5% to about 50% (wt/wt) of the implant.

In embodiment (72), there is provided a formulation of any one of embodiments (68) through (71), wherein the formulation provides a therapeutically effective concentration of dexamethasone for up to about six months, up to about 12 months, up to about 18 months, or up to about 24 months.

In embodiment (73), there is provided a formulation of any one of embodiments (68) through (72), wherein the sustained release occurs over a period of (a) at least about one week, about two weeks, about three weeks, about four weeks, about one month, about two months, about three months, about four months, about five months after administering the implant to the fat pad; or (b) up to about 6 months, up to about 12 months, about 18 months, or about 24 months after administering the implant to the joint fat pad; or (c) any period of time specified in (a) or (b), for example, at least about 6 months; or (d) any combination of each period of time specified in (a) and (b), for example, for at least about one month and up to about 18 months.

In embodiment (74), there is provided a formulation of any one of embodiments (68) through (73), wherein the formulation provides at least one of reduced systemic exposure, reduced side effects, enhanced dosing precision, and reduced frequency of administration, wherein each reduction or enhancement is relative to a systemic or an intra-articular administration of a therapeutic dose, such as a routine therapeutic dose, of dexamethasone.

In embodiment (75), there is provided the formulation of any one of embodiments (68) through (74), wherein a single administration of the formulation to the joint fat pad provides equivalent or superior relief of the pain, inflammation or disease of the joint relative to a single systemic or intra-articular administration of a therapeutic dose, such as a routine therapeutic dose, of dexamethasone.

In embodiment (76), there is provided the formulation of any one of embodiments (68) through (75), wherein a single administration of the formulation to the joint fat pad provides reduced systemic exposure and equivalent or superior relief of the pain, inflammation or disease of the joint relative to a single systemic or intra-articular administration of a therapeutic dose, such as a routine therapeutic dose, of dexamethasone.

In embodiment (77), there is provided a method of treating pain, inflammation, or disease in a joint of a subject, the method comprising administering a formulation of any one of embodiments (68)-(76) to a fat pad of the joint.

In embodiment (78), there is provided the method of embodiment (77), wherein the method provides a therapeutically effective amount of the dexamethasone, thereby relieving the joint from pain, inflammation or disease.

In embodiment (79), there is provided the method of embodiment (77) or (78), wherein the joint is an arthritic joint, an injured joint or a surgically replaced joint.

In embodiment (80), there is provided the method of any one of embodiments (77) through (79), wherein the joint is a synovial joint.

In embodiment (81), there is provided the method of any one of embodiments (77) through (80), wherein the joint is a knee joint, and the fat pad is an infrapatellar fat pad, a suprapatellar fat pad, or an anterior femoral fat pad of the knee joint.

In embodiment (82), there is provided the method of any one of embodiments (77) through (81), wherein the administering comprises injecting, embedding or implanting the implant into the fat pad.

In embodiment (83), there is provided the method of any one of embodiments (77) through (82), wherein the pain, inflammation or disease is associated with osteoarthritis, rheumatoid arthritis, juvenile arthritis, calcium pyrophosphate dehydrate crystal deposition disease (CPPD, or pseudo gout), post-operative pain, joint replacement surgery pain or a combination thereof.

In embodiment (84), there is provided the method of any one of embodiments (77) through (83), wherein the method relieves the joint from the pain, inflammation, or disease for a period of (a) at least about one week, about two weeks, about three weeks, about four weeks, about one month, about two months, about three months, about four months, about five months after administering the implant to the fat pad; or (b) up to about 6 months, up to about 12 months, about 18 months, or about 24 months after administering the implant to the joint fat pad; or (c) any period of time specified in (a) or (b), for example, at least about 6 months; or (d) any combination of each period of time specified in (a) and (b), for example, for at least about one month and up to about 18 months.

In embodiment (85), there is provided the method of any one of embodiments (77) through (84), the method providing at least one of reduced systemic exposure, reduced side effects, enhanced dosing precision, and reduced frequency of administration; wherein each reduction or enhancement is relative to a systemic or intra-articular administration of a therapeutic dose, such as a routine therapeutic dose, of the dexamethasone.

In embodiment (86), there is provided the method of any one of embodiments (77) through (85), wherein the treating comprises one or more administrations of the implant to the joint fat pad.

In embodiment (87), there is provided the method of any one of embodiments (77) through (86), wherein the treating comprises a single administration of the implant to the joint fat pad.

In embodiment (88), there is provided the method of embodiment (87), wherein the single administration provides a therapeutically effective amount of the dexamethasone to the joint, thereby relieving the joint from the pain, inflammation or disease.

In embodiment (89), there is provided the method of embodiment (87) or (88), wherein the single administration of the implant to the joint fat pad relieves the joint from the pain, inflammation, or disease for a period of (a) at least about one week, about two weeks, about three weeks, about four weeks, about one month, about two months, about three months, about four months, about five months after administering the implant to the fat pad; or (b) up to about 6 months, up to about 12 months, about 18 months, or about 24 months after administering the implant to the joint fat pad; or (c) any period of time specified in (a) or (b), for example, at least about 6 months; or (d) any combination of each period of time specified in (a) and (b), for example, for at least about one month and up to about 18 months.

In embodiment (90), there is provided the method of any one of embodiments (87) through (89), wherein the single administration of the implant to the joint fat pad delivers the therapeutically effective amount of the dexamethasone with reduced systemic exposure or reduced side effects relative to a single systemic or a single intra-articular administration of a therapeutic dose, such as a routine therapeutic dose, of dexamethasone.

In embodiment (91), there is provided the method of any one of embodiments (87) through (90), wherein the single administration of the implant to the joint fat pad provides equivalent or superior relief of the pain, inflammation or disease of the joint relative to a single systemic or intra-articular administration of a therapeutic dose, such as a routine therapeutic dose, of dexamethasone.

In embodiment (92), there is provided the method of any one of embodiments (87) through (91), wherein a single administration of the implant to the joint fat pad provides reduced systemic exposure and equivalent or superior relief of the pain, inflammation or disease of the joint relative to a single systemic or intra-articular administration of a therapeutic dose, such as a routine therapeutic dose, of dexamethasone.

In embodiment (93), there is provided the formulation of any one of embodiments (1) through (23), (39) through (49), and (66) through (76), further comprising an anesthetic agent.

In embodiment (94), there is provided the formulation of embodiment (93), wherein the anesthetic is selected from lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, combinations thereof, and salts thereof.

In embodiment (95), there is provided the formulation of any one of embodiments (1) through (23), (39) through (49), and (66) through (76), and (94), wherein the anesthetic is lidocaine.

In embodiment (96), there is provided the formulation according to embodiment (1) through (23), (39) through (49), (66) through (76), and (93) through (95), wherein the formulation provides sustained release of the therapeutic agent to the joint cavity and surrounding tissues.

In embodiment (97), there is provided the formulation according to any one of embodiments (1) through (23), (39) through (49), (66) through (76), and (93) through (96), wherein the formulation is administered and retained in the fat pad without a member for anchoring the formulation to the fat pad or other joint tissue.

In embodiment (98), there is provided the method of one of embodiments (24) through (38), (50) through (65), and (77) through (94), wherein the formulation is administered and retained in the fat pad without introducing a member for anchoring the formulation to the fat pad or other joint tissue.

In embodiment (99), there is provided the method according to embodiment (98), wherein the other joint tissue is selected from a bursa, a synovial membrane, a gutter, cartilage and a second fat pad of the joint.

In embodiment (100), there is provided the method according to embodiment (99), wherein said member comprises a staple, stich, suture, barb, hook, screw, tether, clip, tape, wire, expandable memory alloy, adhesive or combination thereof.

In embodiment (101), there is provided: A formulation for use in treating pain, inflammation, disease, or a combination thereof, in a joint of a subject in need of such treatment, by administering the formulation to a fat pad of the joint of the subject, wherein the formulation comprises:
  a therapeutic agent selected from an analgesic agent, an anti-inflammatory agent, an immunosuppressive agent, and combinations thereof;
  wherein the formulation provides sustained release of the therapeutic agent to the joint.

In embodiment (102), there is provided: The formulation for use according to embodiment (101), wherein the formulation provides a therapeutically effective amount of the therapeutic agent, thereby relieving the joint from the pain, inflammation, disease, or combination thereof.

In embodiment (103), there is provided: The formulation for use according to embodiment (101) or (102), wherein the therapeutic agent is an anti-inflammatory agent.

In embodiment (104), there is provided: The formulation for use according to any one of embodiments (101) through (103), wherein the anti-inflammatory agent is selected from the group consisting of steroidal anti-inflammatory agents, non-steroidal anti-inflammatory agents (NSAIDs), anti-inflammatory cytokines, antimetabolites, N-methyl-D-aspartate (NMDA) receptor antagonists, and combinations thereof.

In embodiment (105), there is provided: The formulation for use according to any one of embodiments (101) through (104), wherein the therapeutic agent is selected from antagonists of interleukin (IL) receptors IL-1, IL-4, IL-6, IL-11, and IL-13; pro-inflammatory cytokine inhibitors such as tumor necrosis factor-alpha (TNF-α) and IL-18; and antimetabolites such as antifolates.

In embodiment (106), there is provided: The formulation for use according to embodiment (101) or (102), wherein the therapeutic agent is an immunosuppressive agent.

In embodiment (107), there is provided: The formulation for use according to any one of embodiments (101), (102) and (106), wherein the therapeutic agent is an immunosuppressive agent selected from the group consisting of azathioprine, cyclosporine, mizoribine, tacrolimus, derivatives of the foregoing, and combinations thereof in embodiment (107a), the therapeutic agent is cyclosporine A.

In embodiment (108), there is provided: The formulation for use according to embodiment (101) or (102), wherein the therapeutic agent is an analgesic agent.

In embodiment (109), there is provided: The formulation for use according to any one of embodiments (101), (102) and (108), wherein the therapeutic agent is an analgesic agent selected from acetaminophen (paracetamol), opiates, non-steroidal anti-inflammatory agents (NSAIDS), steroidal anti-inflammatory agents, cyclooxygenase-2 (COX2) inhibitors, N-methyl-D-aspartate receptor (NMDA) receptor antagonists, derivatives of the foregoing, and combinations thereof.

In embodiment (110), there is provided: The formulation for use according to any one of embodiments (101), (102), (108) and (109), wherein the therapeutic agent is an analgesic agent which is acetaminophen (paracetamol).

In embodiment (111), there is provided: The formulation for use according to any one of embodiments (101), (102), (108) and (109), wherein the therapeutic agent is an analgesic agent which is an opiate.

In embodiment (112), there is provided: The formulation for use according to any one of embodiments (101), (102), (108), (109) and (111), wherein the therapeutic agent is an analgesic agent which is an opiate selected from codeine, morphine, dihydromorphine, fentanyl, hydrocodone, oxycodone, pethidine, methadone, dextropropoxyphene, buprenorphine, tramadol and ketobemidone.

In embodiment (113), there is provided: The formulation for use according to any one of embodiments (101) through (104), (108) and (109), wherein the therapeutic agent is a NSAID.

In embodiment (114), there is provided: The formulation for use according to any one of embodiments (101) through (104), (108), (109) and (113), wherein the therapeutic agent is NSAID selected from aspirin, diclofenac, diflunisal, etodolac, ibuprofen, indomethacin, ketoprofen, ketorolac, nabumetone, naproxen, oxaprozin, piroxicam, salsalate, sulindac, tolmetin, and agents that selectively block cyclooxygenase-2 (COX-2); in further embodiment (114a), the therapeutic agent is a COX-2 inhibitor selected from celecoxib, valdecoxib and rofecoxib.

In embodiment (115), there is provided: The formulation for use according to any one of embodiments (101) through (104), (108) and (109), wherein the therapeutic agent is a N-methyl-D-aspartate receptor (NMDA) receptor antagonist.

In embodiment (116), there is provided: The formulation for use according to any one of embodiments (101) through (104), (108), (109) and (115), wherein the therapeutic agent is a N-methyl-D-aspartate methyl-D-aspartate receptor (NMDA) receptor antagonist selected from AP5 (APV, R-2-amino-5-phosphonopentanoate), AP7 (2-amino-7-phosphonoheptanoic acid), CPPene (3-[(R)-2-carboxypiperazin-4-yl]-prop-2-enyl-1-phosphonic acid), selfotel, amantadine, atomoxetine, AZD6765, dextrallorphan, dextromethorphan, dextrorphan, diphenidine, dizocilpine (MK-801), eticyclidine, gacyclidine, ibogaine, magnesium, memantine, methoxetamine, nitromemantine, nitrous oxide, phencyclidine, rolicyclidine, tenocyclidine, methoxydine, tiletamine, xenon, neramexanee, etoxadrol, dexoxadrol, WMS-2539, NEFA, remacemide, delucemine, 8A-PDHQ, aptiganel, HU-211, remacemide, rhynchophylline, ketamine, GLYX-13, TK-40, 1-aminocyclopropanecarboxylic acid, 7-chlorokynurenic acid, DCKA (5,7-dichlorokynurenic acid), kynurenic acid, lacosamide and L-phenylalanine.

In embodiment (117), there is provided: The formulation for use according to any one of embodiments (101) through (104), (108) and (109), wherein the therapeutic agent is a steroidal anti-inflammatory agent.

In embodiment (118), there is provided: The formulation for use according to any one of embodiments (101) through (104), (108), (109) and (117), wherein the therapeutic agent is a steroidal anti-inflammatory agent selected from 21-acetoxypregnenolone, alclometasone, alclometasone dipropionate, algestone, amcinonide, beclomethasone, betamethasone, betamethasone dipropionate, betamethasone sodium phosphate, betamethasone valerate, budesonide, chloroprednisone, ciclesonide, clobetasol, clobetasol-17-propionate, clobetasone-17-butyrate, clobetasone, clocortolone, cloprednol, corticosterone, cortisone, cortisone acetate, cortivazol, deflazacort, desonide, desoximetasone, dexamethasone, dexamethasone sodium phosphate, diflorasone, diflucortolone, difluprednate, enoxolone, fluazacort, fluclo ronide, flumethasone, fluocinonide, fluocinolone, fluocinolone acetonide, fluocinonide, fluocortin butyl, fluocortolone, fluocortolone caproate, fluocortolone pivalate, fluorometholone, flunisolide, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, hydrocortisone acetate, hydrocortisone-17-aceponate, hydrocortisone-17-buteprate, hydrocortisone-17-butyrate, hydrocortisone-17-valerate, loteprednol, mazipredone, medrysone, meprednisone, methylprednisolone, mometasone, mometasone furoate, paramethasone, paramethasone acetate, prednicarbate, prednisolone, prednisolone 25-diethylamino-acetate, prednisolone sodium phosphate, prednisone, prednival, prednylidene, rimexolone, tixocortol, tixocortol pivalate, triamcinolone, triamcinolone acetonide, triamcinolone alcohol, triamcinolone benetonide, triamcinolone hexacetonide, derivatives of the foregoing, salts of the foregoing, and mixtures of the foregoing.

In embodiment (119), there is provided: The formulation for use according to any one of embodiments (101) through (104), (108), (109), (117) and (118), wherein the therapeutic agent is dexamethasone.

In embodiment (120), there is provided: The formulation for use according to any one of embodiments (101) through (119), wherein the formulation is provided as a gel, an implant, a silk fibroin hydrogel, microspheres, nanospheres or liposomes.

In embodiment (121), there is provided: The formulation for use according to any one of embodiments (101) through (120), wherein the formulation is provided as microspheres, nanospheres, or an implant; in embodiment (121a), the microspheres, nanospheres or implant comprises a polymer; in embodiment (121b), the polymer is a biodegradable polymer; in embodiment (121c), the polymer is selected from the group consisting of poly(D,L-lactide-co-glycolide), poly (D,L-lactide), poly(ethylene glycol), poly(propylene fumarate), poly(vinyl alcohol), poly(dioxanone), poly (caprolactone), poly(propylene fumarate), poly(propylene oxide), polyanhydrides, polyphosphazenes, polysaccharides, proteins, and combinations thereof; in embodiment (121d), the formulation is provided as microspheres comprising a biodegradable polymer selected from the group consisting of poly(D,L-lactide-co-glycolide), poly (D,L-lactide), poly(caprolactone) and combinations thereof; in embodiment (121e), the formulation is provided as nanospheres comprising a biodegradable polymer selected from the group consisting of poly(D,L-lactide-co-glycolide), poly (D,L-lactide), poly(caprolactone) and combinations thereof; in embodiment (121f), the formulation is provided as an implant comprising a biodegradable polymer selected from the group consisting of poly(D,L-lactide-co-glycolide), poly (D,L-lactide), poly(caprolactone) and combinations thereof; in embodiment (121 g), the formulation is provided as a solid implant comprising a biodegradable polymer selected from the group consisting of poly(D,L-lactide-co-glycolide), poly (D,L-lactide), poly(caprolactone) and combinations thereof; in embodiment (121h), the formulation is provided as an implant wherein the polymer is poly(D,L-lactide-co-glycolide).

In embodiment (122), there is provided: The formulation for use according to embodiment (121), wherein the polymer comprises a polysaccharide selected from agarose, alginate (such as calcium alginate), chitosan, carboxymethylcellulose, hyaluronic acid and combinations thereof; in embodiment (122a), the polysaccharide is hyaluronic acid; in embodiment (122b), the hyaluronic acid is crosslinked; in embodiment (122c), the hyaluronic acid is noncrosslinked.

In embodiment (123), there is provided: The formulation for use according to embodiments (121), wherein the polymer comprises a protein selected from collagen, gelatin, fibrin, and a combination thereof; in embodiment (123a), the protein is collagen.

In embodiment (124), there is provided: The formulation for use according to any one of embodiments (101) through (120), wherein the formulation is provided as a gel; in further embodiment (124a), the gel is a gel solution or gel suspension; in embodiment (124b), the gel a hydrogel; in embodiment (124c), the gel is a silk fibroin hydrogel.

In embodiment (125), there is provided: The formulation for use according to embodiment (124), wherein the gel comprises a polysaccharide, a protein or a combination thereof.

In embodiment (126), there is provided: The formulation for use according to embodiment (125), wherein gel comprises hyaluronic acid; in embodiment (126a), the hyaluronic acid is crosslinked; in embodiment (126b), the hyaluronic acid is noncrosslinked.

In embodiment (127), there is provided: The formulation for use according to embodiment (125), wherein the gel comprises a protein selected from collagen, gelatin, fibrin, and a combination thereof.

In embodiment (128), there is provided: The formulation for use according to embodiment (125), where the gel comprises a polysaccharide and a protein; in embodiment 128(a), the polysaccharide is crosslinked to the protein.

In embodiment (129), there is provided: The formulation for use according to embodiment (128), wherein the polysaccharide is hyaluronic acid and the protein is collagen.

In embodiment (130), there is provided: The formulation for use according to any one of embodiments (124) through (129), wherein the therapeutic agent is incorporated into a biocompatible and biodegradable vessel, said vessel selected from liposomes, micelles, and polymerized vesicles, wherein said vessels are incorporated into the gel.

In embodiment (131), there is provided: The formulation for use according to any one of embodiments (101) through (130), wherein the joint is an arthritic joint, an injured joint or a surgically replaced joint.

In embodiment (132), there is provided: The formulation for use according to any one of embodiments (101) through (131), wherein the joint is a synovial joint.

In embodiment (133), there is provided: The formulation for use according to any one of embodiments (101) through (132), wherein the joint is a knee joint; in embodiment (133a), the fat pad is an infrapatellar fat pad, a suprapatellar fat pad, or an anterior femoral fat pad.

In embodiment (134), there is provided: The formulation for use according to any one of embodiments (101) through (133), wherein the joint is a knee joint, and the fat pad is an infrapatellar fat pad.

In embodiment (135), there is provided: The formulation for use according to any one of embodiments (101) through (134), wherein the sustained release occurs over a period of at least about one week, about two weeks, about three weeks, about four weeks, about one month, about two months, about three months, about four months, about five months after administering the formulation to the fat pad.

In embodiment (136), there is provided: The formulation for use according to any one of embodiments (101) through (135), wherein the sustained release occurs over a period of up to about 6 months, about 12 months, about 18 months, or about 24 months after administering the formulation to the joint fat pad; in embodiment (136a), the sustained release occurs over a period of up to about 6 months.

In embodiment (137), there is provided: The formulation for use according to any one of embodiments (101) through (134), wherein the sustained release occurs over a period of up to about 6 to about 24 months, about 6 to about 18 months, about 6 to about 12 months, about 12 to about 24 months, about 12 to about 18 months, or at least about 12 months.

In embodiment (138), there is provided: The formulation for use according to any one of embodiments (101) through (137), providing at least one of reduced systemic exposure, reduced side effects, enhanced dosing precision, and reduced frequency of administration, wherein each reduction or enhancement is relative to a systemic or an intra-articular administration of a therapeutic dose, such as a routine therapeutic dose, of the therapeutic agent.

In embodiment (139), there is provided: The formulation for use according to any one of embodiments (101) through (138), wherein a single administration of the formulation to the joint fat pad provides equivalent or superior relief of the pain, inflammation or disease of the joint relative to a single systemic or intra-articular administration of a therapeutic dose, such as a routine therapeutic dose, of the therapeutic agent.

In embodiment (140), there is provided: The formulation for use according to any one of embodiments (101) through (139), comprising one or more administrations of the formulation to the joint fat pad.

In embodiment (141), there is provided: The formulation for use according to any one of embodiments (101) through (140), comprising a single administration of the formulation to the joint fat pad.

In embodiment (142), there is provided: The formulation for use according to any one of embodiments (101) through (141), wherein the administering comprises injecting, embedding or implanting the formulation into the joint fat pad.

In embodiment (143), there is provided: The formulation for use according to any one of embodiments (101) through (142), wherein the pain, inflammation or disease is associated with osteoarthritis, rheumatoid arthritis, juvenile arthritis, calcium pyrophosphate dehydrate crystal deposition disease (CPPD, or pseudo gout), post-operative pain, joint replacement surgery pain or a combination thereof.

In embodiment (144), there is provided: The formulation for use according to any one of embodiments (101) through (143), wherein the pain, inflammation or disease is associated with osteoarthritis.

In embodiment (145), there is provided: The formulation for use according to any one of embodiments (101) through (144), further comprising an anesthetic agent.

In embodiment (146), there is provided: The formulation for use according to any one of embodiments (101) through (145), further comprising an anesthetic agent selected from lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, combinations thereof, and salts thereof.

In embodiment (147), there is provided: The formulation for use according to any one of embodiments (101) through (146), wherein the formulation contains lidocaine.

In embodiment (148), there is provided: The formulation for use according to embodiment (119), in which the therapeutic agent is a steroidal anti-inflammatory agent, wherein the therapeutic agent is dexamethasone and the formulation is provided as a gel.

In embodiment (149), there is provided: The formulation for use according to embodiment (148), wherein the formulation is provided as a gel suspension.

In embodiment (150), there is provided: The formulation for use according to embodiment (148) or (149), wherein the gel comprises hyaluronic acid.

In embodiment (151), there is provided: The formulation for use according to any one of embodiments (148) through (150), further comprising an anesthetic agent.

In embodiment (152), there is provided: The formulation for use according to any one of embodiments (148) through (151), further comprising an anesthetic agent selected from lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, combinations thereof, and salts thereof.

In embodiment (153), there is provided: The formulation for use according to any one of embodiments (148) through (152), wherein the formulation contains lidocaine.

In embodiment (154), there is provided: The formulation for use according to any one of embodiments (148) through (153), wherein the dexamethasone is provided at a concentration ranging from about 0.1% to about 50% (wt/wt), about 0.5% to about 30% (wt/wt), about 1% to about 25% (wt/wt), or about 2% to about 20% (wt/wt) of the formulation.

In embodiment (155), there is provided: The formulation for use according to any one of embodiments (148) through (154), wherein the dexamethasone is provided at a concentration of about 2%, about 10% or about 20% (wt/wt) of the formulation; in embodiment (155a), the dexamethasone is provided at a concentration of about 2%, about 10% or about 20% (wt/wt), of the formulation.

In embodiment (156), there is provided: The formulation for use according to any one of embodiments (148) through (155), wherein the hyaluronic acid is sodium hyaluronan.

In embodiment (157), there is provided: The formulation for use according to any one of embodiments (150) through (156), wherein the hyaluronic acid concentration is about 1% to about 10% (wt/wt), or about 1% to about 5% (wt/wt), or about 2% (wt/wt), of the formulation; in embodiment (157a), the formulation is a gel suspension.

In embodiment (158), there is provided: The formulation for use according to any one of embodiments (148) through (157), wherein the joint is an arthritic joint, an injured joint or a surgically replaced joint.

In embodiment (159), there is provided: The formulation for use according to any one of embodiments (148) through (158), wherein the joint is a synovial joint.

In embodiment (160), there is provided: The formulation for use according to any one of embodiments (148) through (159), wherein the joint is a knee joint; in embodiment (160a), the fat pad is an infrapatellar fat pad, a suprapatellar fat pad, or an anterior femoral fat pad.

In embodiment (161), there is provided: The formulation for use according to embodiment (160), wherein the joint is a knee joint, and the fat pad is an infrapatellar fat pad.

In embodiment (162), there is provided: The formulation for use according to any one of embodiments (148) through (161), wherein the sustained release occurs over a period of at least about one week, about two weeks, about three weeks, about four weeks, about one month, about two months, about three months, about four months, about five months after administering the formulation to the fat pad.

In embodiment (163), there is provided: The formulation for use according to any one of embodiments (148) through (162), wherein the sustained release occurs over a period of up to about 6 months, about 12 months, about 18 months, or about 24 months after administering the formulation to the joint fat pad; in embodiment (136a), the sustained release occurs over a period of up to about 6 months.

In embodiment (164), there is provided: The formulation for use according to any one of embodiments (148) through (163), wherein the sustained release occurs over a period of up to about 6 to about 24 months, about 6 to about 18 months, about 6 to about 12 months, about 12 to about 24 months, about 12 to about 18 months, or at least about 12 months.

In embodiment (165), there is provided: The formulation for use according to any one of embodiments (148) through (164), which delivers pharmacodynamic concentrations of dexamethasone for up to about 6 months.

In embodiment (166), there is provided: The formulation for use according to any one of embodiments (148) through (165), providing at least one of reduced systemic exposure, reduced side effects, enhanced dosing precision, and reduced frequency of administration, wherein each reduction or enhancement is relative to a systemic or an intra-articular administration of a therapeutic dose, such as a routine therapeutic dose, of the therapeutic agent.

In embodiment (167), there is provided: The formulation for use according to any one of embodiments (148) through (166), wherein a single administration of the formulation to the joint fat pad provides equivalent or superior relief of the pain, inflammation or disease of the joint relative to a single systemic or intra-articular administration of a therapeutic dose, such as a routine therapeutic dose, of the therapeutic agent.

In embodiment (168), there is provided: The formulation for use according to any one of embodiments (148) through (167), comprising one or more administrations of the formulation to the joint fat pad.

In embodiment (169), there is provided: The formulation for use according to any one of embodiments (148) through (168), comprising a single administration of the formulation to the joint fat pad.

In embodiment (170), there is provided: The formulation for use according to any one of embodiments (148) through (169), wherein the administering comprises injecting, embedding or implanting the formulation into the joint fat pad.

In embodiment (171), there is provided: The formulation for use according to any one of embodiments (148) through (170), wherein the pain, inflammation or disease is associated with osteoarthritis, rheumatoid arthritis, juvenile arthritis, calcium pyrophosphate dehydrate crystal deposition disease (CPPD, or pseudo gout), post-operative pain, joint replacement surgery pain or a combination thereof.

In embodiment (172), there is provided: The formulation for use according to any one of embodiments (148) through (171), wherein the pain, inflammation or disease is associated with osteoarthritis.

In embodiment (173), there is provided the formulation according to embodiment (101) through (172), wherein the formulation provides sustained release of the therapeutic agent to the joint cavity and surrounding tissues.

In embodiment (174), there is provided: The formulation for use according to any one of embodiments (101) through (173), wherein the formulation is administered and retained in the fat pad without introducing a member for anchoring the formulation to the fat pad or other joint tissue.

In embodiment (175), there is provided: The formulation for use according to embodiments (174), wherein the other joint tissue is selected from a bursa, a synovial membrane, a gutter, cartilage and a second fat pad of the joint.

In embodiment (176), there is provided: The formulation for use according to embodiment (175), wherein said member comprises a staple, stich, suture, barb, hook, screw, tether, clip, tape, wire, expandable memory alloy, adhesive or combination thereof.

In other aspects, the invention includes:

1. A formulation for administration to a joint fat pad of a subject, the formulation comprising:
    a therapeutic agent selected from an analgesic agent, an anti-inflammatory agent, an immunosuppressive agent, and combinations thereof;
    wherein the formulation provides sustained release of the therapeutic agent to the joint.
2. Formulation 1, wherein the formulation provides a therapeutically effective amount of the therapeutic agent, thereby relieving the joint from pain, inflammation or disease.
3. Formulation 1, wherein the joint is an arthritic joint, an injured joint or a surgically replaced joint.
4. Formulation 1, wherein the joint is a synovial joint.
5. Formulation 1, wherein the joint is a knee joint, and the fat pad is an infrapatellar fat pad, a suprapatellar fat pad, or an anterior femoral fat pad.
6. Formulation 1, wherein the therapeutic agent is an anti-inflammatory agent selected from the group consisting of steroidal anti-inflammatory agents, non-steroidal anti-inflammatory agents (NSAIDs), anti-inflammatory cytokines, antimetabolites, N-Methyl-D-aspartate (NMDA) receptor antagonists, and combinations thereof.
7. Formulation 1, wherein the anti-inflammatory agent is a steroidal anti-inflammatory agent selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, fluocinonide, fluocinolone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol, mazipredone, medrysone, meprednisone, methylprednisolone, mometasone furoate, paramethasone, paramethasone acetate, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, derivatives of the foregoing, and combinations thereof.
8. Formulation 1, wherein the therapeutic agent is an immunosuppressive agent selected from the group consisting of azathioprine, cyclosporine, mizoribine, tacrolimus, derivatives of the foregoing, and combinations thereof.
9. Formulation 1, wherein the therapeutic agent is an analgesic selected from acetaminophen (paracetamol), opiates, non-steroidal anti-inflammatory agents (NSAIDS), steroidal anti-inflammatory agents, cyclooxygenase-2 (COX2) inhibitors, N-Methyl-D-aspartate receptor (NMDA) receptor antagonists, derivatives of the foregoing, and combinations thereof.
10. Formulation 1, wherein the formulation is provided as a gel, an implant, a silk fibroin hydrogel, microspheres, nanospheres or liposomes.
11. Formulation 10, wherein the formulation is provided as a solid implant comprising a biodegradable polymer selected from the group consisting of poly(D,L-lactide-co-glycolide), poly (D,L-lactide), poly(ethylene glycol), poly(propylene fumarate), poly(vinyl alcohol), poly(propylene oxide), polyanhydrides, polyphosphazenes, polysaccharides, proteins, and combinations thereof.
12. Formulation 10, wherein the formulation is provided as a gel suspension comprising hyaluronic acid.
13. Formulation 10, wherein the sustained release occurs over a period of at least about one week, at least about two weeks, at least about three weeks, at least about four weeks, at least about one month, at least about two months, at least about three months, at least about four months, at least about five months or at least about six months after administering the formulation to the fat pad.
14. Formulation 10, wherein the sustained release occurs over a period of up to about 6 to 24 months, about 6 to 18 months, or about 12 to 18 months.
15. Formulation 1, providing at least one of reduced systemic exposure, reduced side effects, enhanced dosing precision, and reduced frequency of administration, wherein each reduction or enhancement is relative to a systemic or an intra-articular administration of a therapeutic dose of the therapeutic agent.
16. Formulation 2, wherein a single administration of the formulation to the joint fat pad provides equivalent or superior relief of pain, inflammation or disease of the joint relative to a single systemic or intra-articular administration of a therapeutic dose of the therapeutic agent.
17. A method of treating pain, inflammation, or disease in a joint of a subject, the method comprising administering Formulation 1 to a fat pad of the joint.
18. Method 17, wherein the method provides a therapeutically effective amount of the therapeutic agent, thereby relieving the joint from the pain, inflammation or disease.

19. Method 17, wherein the joint is an arthritic, injured joint or a surgically replaced joint.
20. Method 17, wherein the joint is a synovial joint.
21. Method 17, wherein the joint is a knee joint, and the fat pad is an infrapatellar fat pad, a suprapatellar fat pad, or an anterior femoral fat pad of the knee joint.
22. Method 17, wherein the administering comprises injecting, embedding, or implanting the formulation into the fat pad.
23. Method 18, wherein the pain, inflammation or disease is associated with osteoarthritis, rheumatoid arthritis, juvenile arthritis, calcium pyrophosphate dehydrate crystal deposition disease (CPPD, or pseudo gout), post-operative pain, joint replacement surgery pain or a combination thereof.
24. Method 18, wherein the method relieves the joint from the pain, inflammation, or disease for a period of (a) at least about one week, about two weeks, about three weeks, about four weeks, about one month, about two months, about three months, about four months, about five months or about six months after administering the formulation to the joint fat pad; or (b) up to about 12 months, about 18 months, or about 24 months after administering the formulation to the joint fat pad; or both.
25. Method 17, providing at least one of reduced systemic exposure, reduced side effects, enhanced dosing precision, and reduced frequency of administration; wherein each reduction or enhancement is relative to a systemic or intra-articular administration of a therapeutic dose of the therapeutic agent.
26. Method 17, wherein the treating comprises one or more administrations of the formulation to the joint fat pad.
27. Method 17, wherein the treating comprises a single administration of the formulation to the joint fat pad.
28. Method 17, wherein the single administration to the joint fat pad is sufficient to provide a therapeutically effective amount of the therapeutic agent to the joint, thereby relieving the joint from the pain, inflammation or disease.
29. Method 27, wherein the single administration to the joint fat pad relieves the joint from the pain, inflammation, or disease for a period of (a) at least about one week, about two weeks, about three weeks, about four weeks, about one month, about two months, about three months, about four months, about five months or about six months after administering the formulation to the joint fat pad; or (b) up to about 12 months, about 18 months, or about 24 months after administering the formulation to the joint fat pad; or both.
30. Method 27, wherein the single administration to the joint fat pad delivers a therapeutically effective amount of the therapeutic agent with reduced systemic exposure or reduced side effects relative to a single systemic or a single intra-articular administration of a therapeutic dose of the therapeutic agent.
31. Method 27, wherein the single administration to the joint fat pad provides equivalent or superior relief of the pain, inflammation or disease of the joint relative to a single systemic or intra-articular administration of a therapeutic dose of the therapeutic agent.

EXAMPLES

Example A

In one formulation, a steroid (powder) is combined with a biodegradable polymer (powder) by dry blending the powders. The powder blend is then heated to a temperature at which it softens (but not so high as to degrade the steroid) and formed into an implant by hot melt extrusion, injection molding, or other thermo-forming measures. The steroid implants are then cut to size, terminally sterilized, and implanted into the target fat pad. Steroid is continuously released into the surrounding area for days, weeks, or months. The implant may contain from 0.1%-70% steroid by weight.

Example B

In another formulation, the steroid is mixed with sterile buffered water to form a slurry. The sterile slurry is combined with a suspending agent, such as buffer, and the formulation is mixed until the slurry is homogeneously dispersed. Suspensions are aseptically filled into unit dose syringes or into sterile vials. The formulation is injected into the target fat pad and slowly releases steroid days, weeks, or months. Suspensions may contain 0.1% to 50% steroid by weight.

Example C

In another formulation, steroid, biodegradable polymer, and other excipients are dissolved or suspended in a biocompatible solvent. The formulation is sterile filtered, autoclaved, or irradiated for sterility. The solution is filled into a sterile vial or a unit dose syringe. After injection into the fat pad, the biocompatible solvent exits the depot, leaving behind a firm steroid-filled implant. The depot releases steroid for days, weeks, or months, as the polymer bioerodes. Drug loading in solution may range from 0.1% to 50%. Polymer loading in solution may range from 15% to 50%. Excipients may include poly(ethylene glycol), short chain fatty acids, waxes, co-solvents, or other compounds which adjust the hydrophobicity of the depot.

Example D

In another formulation, steroid drug particles or steroid containing microspheres or nanospheres are suspended in a crosslinked hydrogel. The hydrogel suspension is injected into the target location. The cohesivity of the crosslinked hydrogel maintains the location of the drug in the target fat pad. Drug is gradually released from the crosslinked hydrogel. After drug has been released, the hydrogel eventually biodegrades and leaves the target fat pad.

Example E

In another formulation, dexamethasone is combined with poly D,L-lactide-co-glycolide and extruded to provide a bioerodible implant. The implant can be prepared essentially as described in U.S. Pat. No. 8,034,366, which is hereby incorporated by reference in its entirety.

Example 1: Preparation of Formulations

Dexamethasone was prepared as a slurry in phosphate buffer saline (PBS) (see I), which was used to prepare gel suspensions in hyaluronic acid containing 2%, 10%, and 20% dexamethasone in 2% sodium hyaluronate (wt/wt) (see IIA through C), as described below.

I. Preparation of Dexamethasone Slurry (25% dexamethasone, 75% PBS)

1) Added 24.923 g of dexamethasone and 77.146 g of 1×PBS into a Thinky mixing container;

2) Mixed using the Thinky mixer at 2000 rpm for 5 minutes;

3) Transferred the resulting slurry into a 250 mL flask and autoclaved slurry at 121° C. for 15 minutes.

II. Preparation of dexamethasone-hyaluronic Acid (Dex:HA) Formulations

A. Formulation 10680-186-1: 20% dexamethasone, 2% hyaluronic acid (HA)
1) Added 40.18 g of dexamethasone slurry, 9.28 g of 1×PBS, and 1.01 g of hyaluronic acid into a Thinky mixing container;
2) Mixed using the Thinky mixer for 20 minutes at 2000 RPM;
3) Transferred to sterile syringes and stored refrigerated.

B. Formulation 10680-186-2: 10% dexamethasone, 2% HA
1) Added 20.13 g of dexamethasone slurry, 29.09 g of 1×PBS, and 1.07 g of hyaluronic acid into a Thinky mixing container;
2) Mixed using the Thinky mixer for 20 minutes at 2000 RPM;
3) Transferred to sterile syringes and stored refrigerated.

C. Formulation 10680-186-3: 2% dexamethasone, 2%, HA
1) Added 4.00 g of dexamethasone slurry, 45.02 g of 1×PBS, and 1.08 g of hyaluronic acid into a Thinky mixing container;
2) Mixed using the Thinky mixer for 20 minutes at 2000 RPM;
3) Transferred to sterile syringes and stored refrigerated.

Example 2: In Vitro Release of Dexamethasone from Depot Formulations

Figure 2:
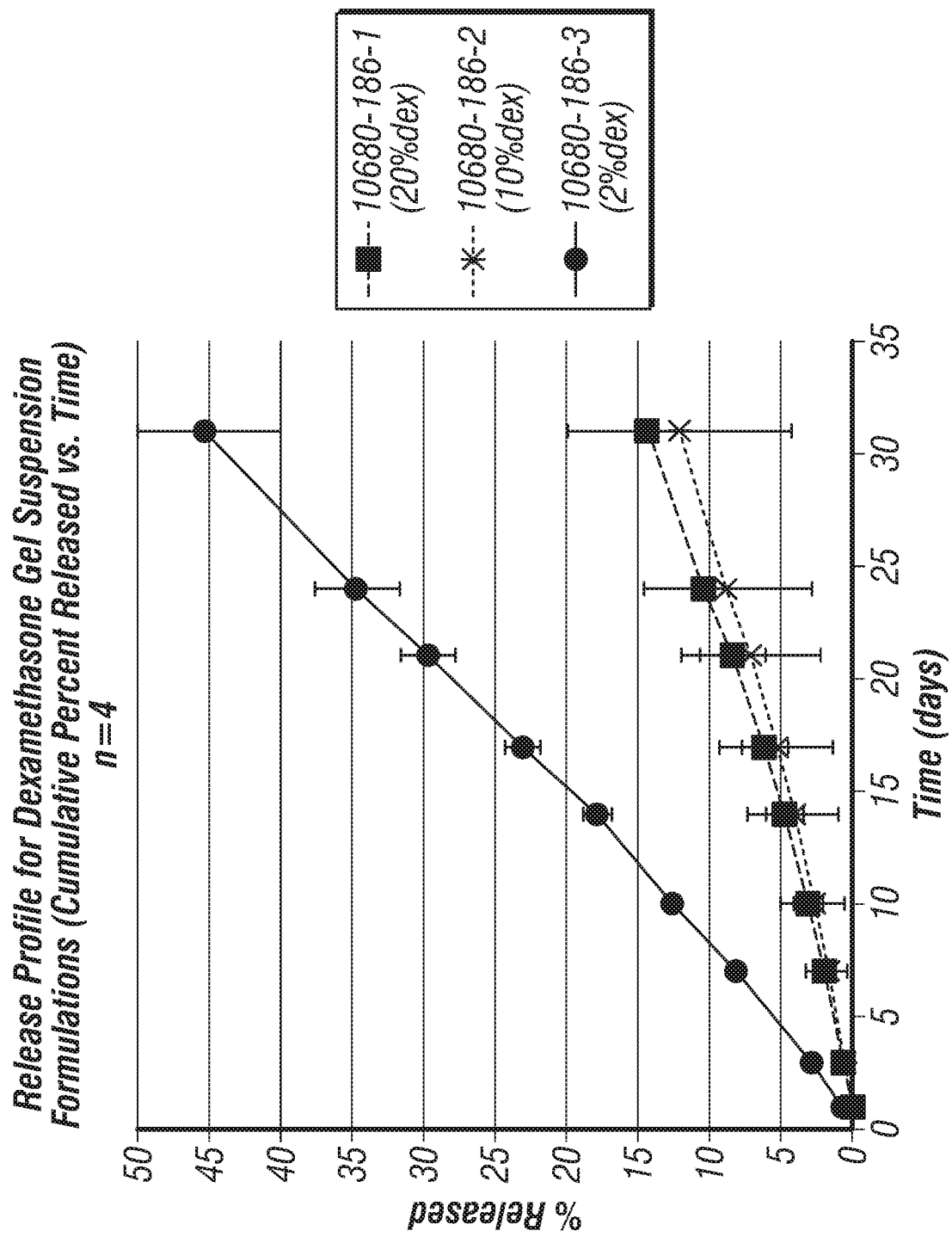
FIG. 2 shows the in vitro cumulative percent dexamethasone released from gel formulations as a function of time into release media (phosphate buffered saline) at 37° C. in a shaking water bath (50 RPM). The gel formulations are 100 µL hyaluronic acid gel suspensions with 2%, 10% or 20% dexamethasone (wt/wt), 2% sodium hyaluronate (wt/wt).
Figure 3:
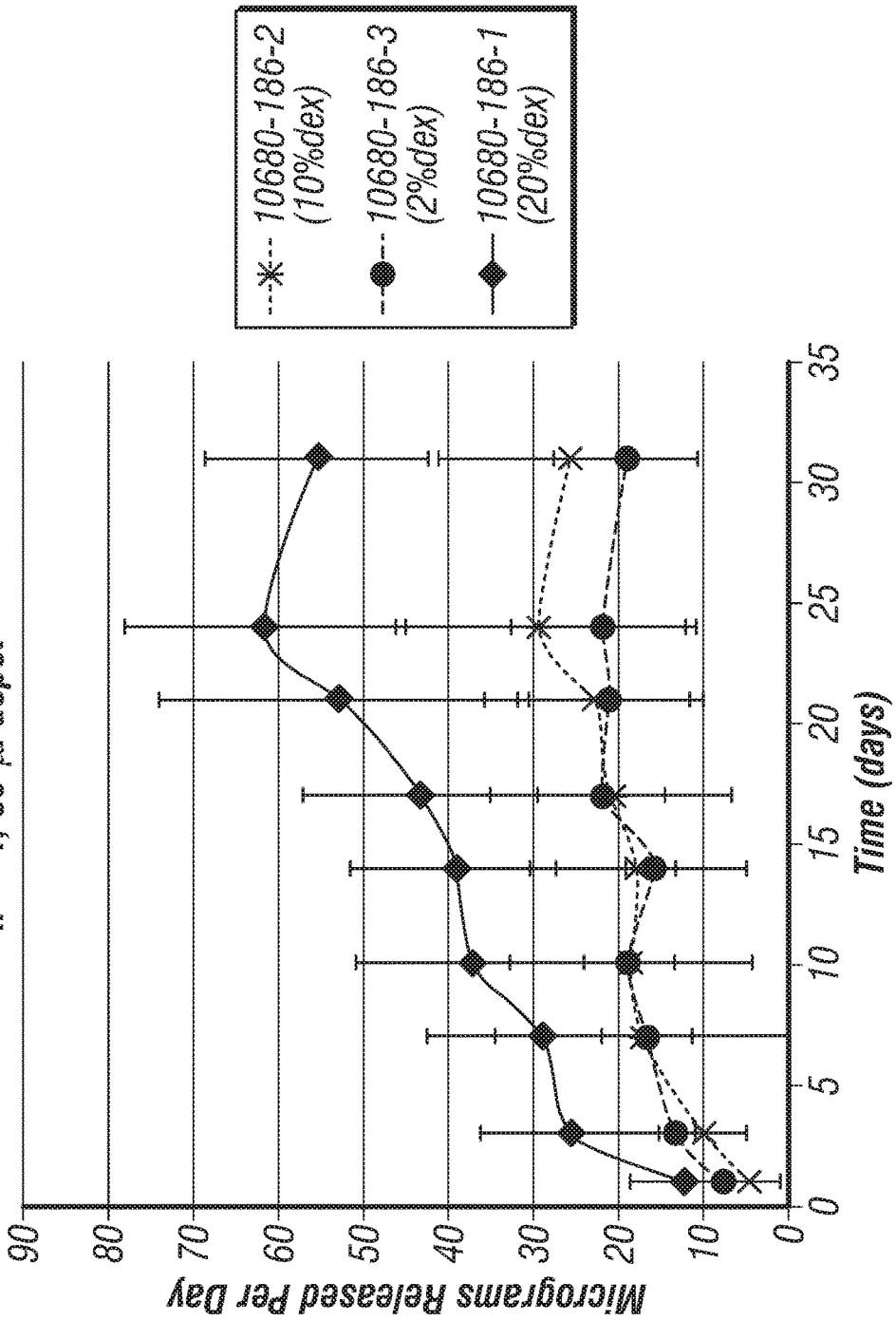
FIG. 3 shows the in vitro amount (micrograms) dexamethasone released from gel formulations per day into release media (phosphate buffered saline) at 37° C. in a shaking water bath (50 RPM). The gel formulations are 50 µL hyaluronic acid gel suspensions with 2%, 10% or 20% dexamethasone (wt/wt), 2% sodium hyaluronate (wt/wt).

The in vitro cumulative release profiles of dexamethasone from the three Dex:HA gel suspensions (as prepared in Example 1) are shown in FIG. 2 (% release as a function of time) and FIG. 3 (micrograms released per day as a function of time). The dexamethasone formulated in hyaluronic acid (Dex:HA formulations) displayed long-lasting delivery in vitro. Based on the data in FIG. 2 and FIG. 3, formulations containing 10% and 20% dexamethasone (wt/wt) may deliver pharmacodynamic concentrations for up to 6 months.

Example 3: In Vivo Delivery and Efficacy of a Formulation Comprising a Dexamethasone-Hyaluronic Gel in the Lipopolysaccharide (LPS)-Induced Model of Synovial Joint Inflammation In vivo delivery and efficacy of Dex:HA gel suspension formulations were tested in the lipopolysaccharide (LPS)-induced model of synovial joint inflammation to mimic the inflammatory pathogenesis of arthritis. Dexamethasone was formulated at 2%, 10% and 20% (wt/wt) in sterile hyaluronic acid gel as described in Example 1. Dexamethasone sodium phosphate injection (Decadron®, Pfizer Injectables; "Dex") was used as a positive control.

Figure 4:
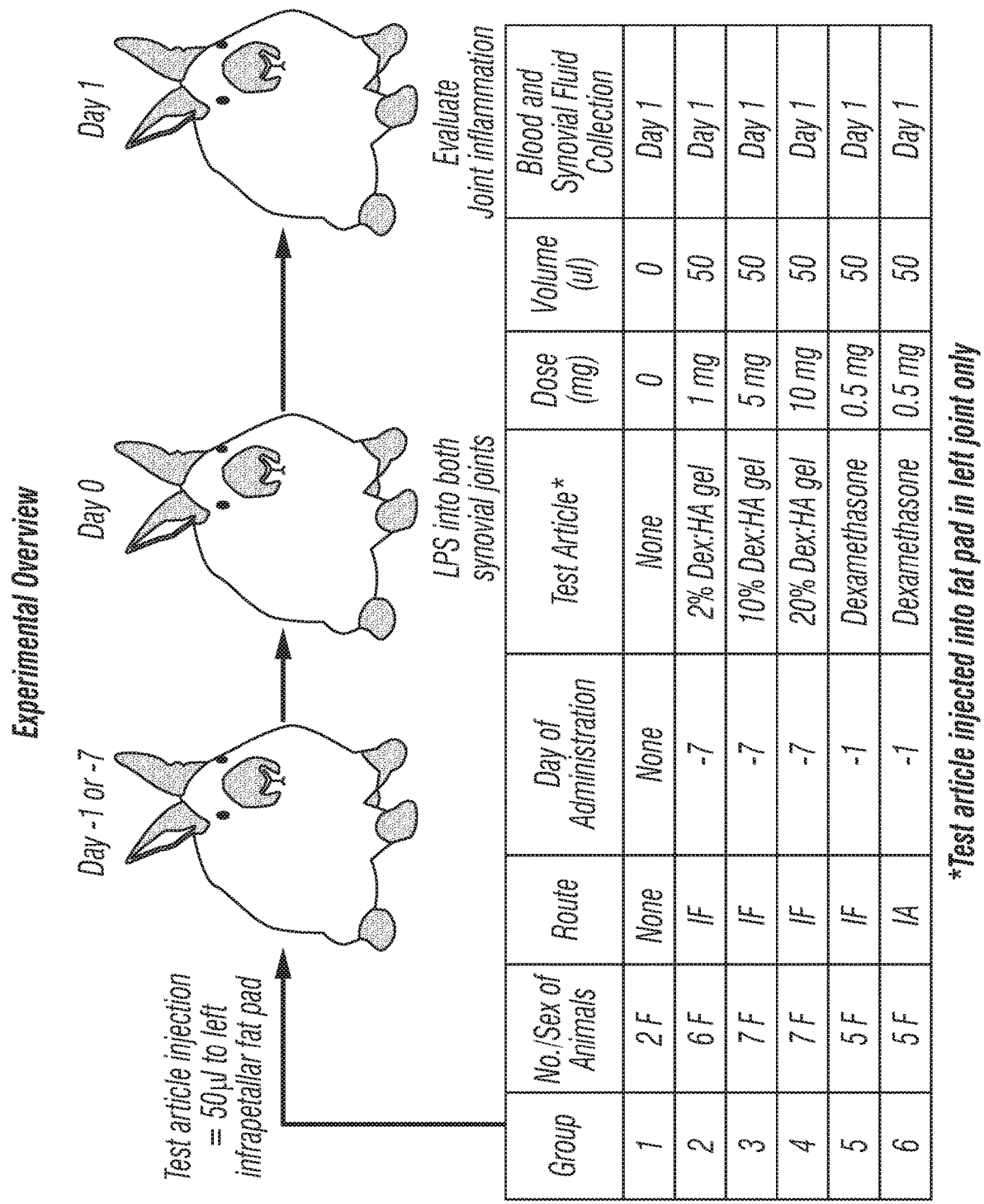
FIG. 4 shows an overview of the experimental model for determining in vivo delivery, efficacy, and pharmacokinetics of dexamethasone sustained release formulations (Dex:HA) versus injection of dexamethasone sodium phosphate injection (Decadron®, Pfizer Injectables; "Dex") in a synovial joint rabbit model. N=32.

The in vivo study (see FIG. 4 for study design overview) was conducted in 32 female New Zealand White rabbits (~3 kg each). Two rabbits were naïve controls. In the other 30 rabbits, a 50 µl A dexamethasone:hyaluronic acid gel injection (Dex:HA; 2%, 10% and 20% (1 mg, 5 mg and 10 mg, respectively) was delivered to the left knee joints, specifically within the infrapatellar fat pad, at Day −7. As comparators, 50 µl A (0.5 mg) of the positive control (Dex) was delivered to the infrapatellar fat pad (Dex-IF) or by intra-articular injection (Dex-IA) at Day −1.

Disease severity and pharmacokinetics were evaluated 7 days after Dex:HA gel suspension injection or 24 hours after Dex (positive control) injections. Before that point, inflammation was induced on Day 0 by injecting LPS into the synovial space of both knee joints, and inflammation was subsequently evaluated 1 day later. Rabbits were sacrificed and evaluated for inflammation by quantifying inflammatory cells (heterophils=neutrophils) in the synovial fluid. In addition, blood, fat pad and synovial fluid were collected for pharmacokinetic analysis, to determine the relative drug tissue levels.

Figure 5A:
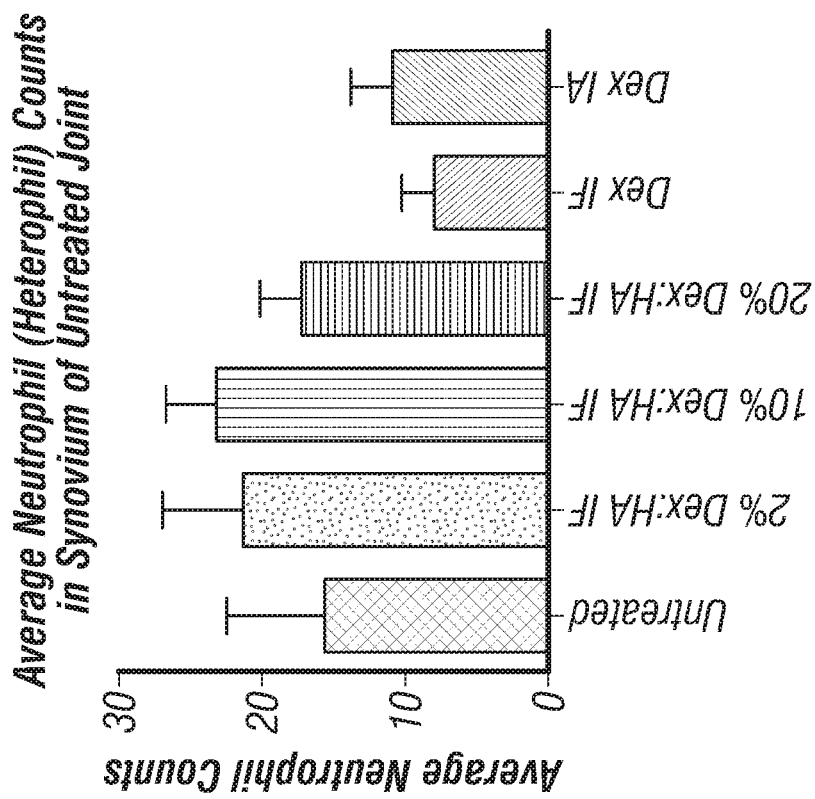
FIG. 5A) Average neutrophil (heterophil) counts in synovium of joints untreated or treated with a 50 µL depot of dexamethasone:hyaluronic acid (Dex:HA) gel suspension containing 2%, 10% or 20% dexamethasone (wt/wt), versus intra-articular (IA) or intra-fat pad (IF) injection of dexamethasone sodium phosphate injection (Dex).

As shown in FIG. 5, infrapatellar fat pad delivery (IF) of sustained release dexamethasone gel suspension (Dex:HA) resulted in a localized decrease in synovial joint inflammation. Treatment with Dex:HA gel at Day −7 resulted in a dose-dependent decrease in the average number of infiltrating neutrophils (heterophils) within the synovial space (FIG. 5A). A suspension of 20% Dex:HA delivered 7 days prior to LPS injection (Day −7) showed similar efficacy to Dex (positive control) injected in the fat pad or intra-articular space one day prior to LPS injection (Day −1).

Figure 5B:
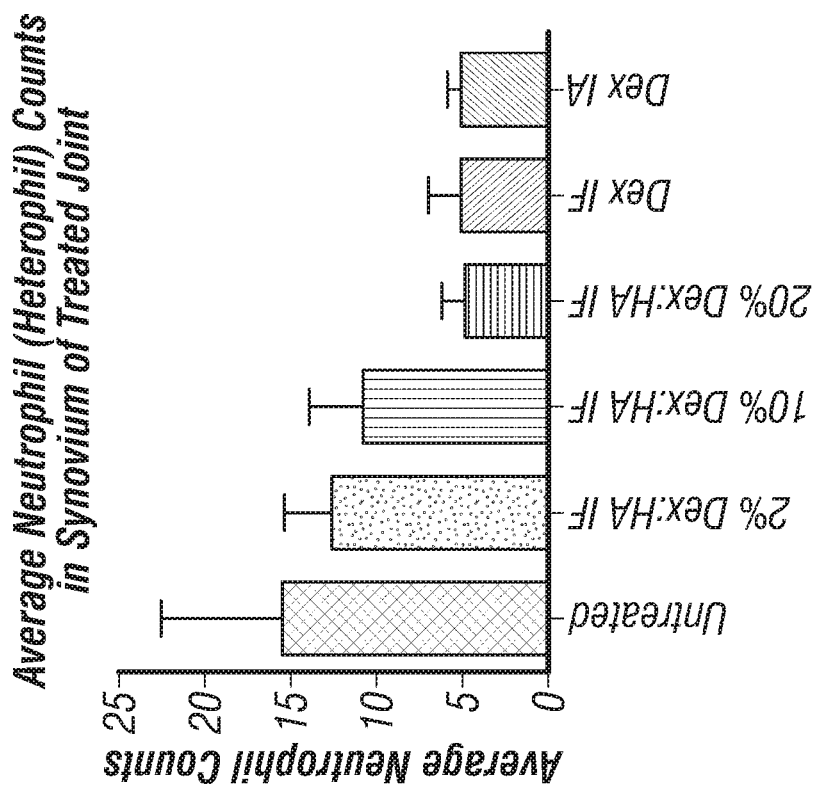
FIG. 5B) Average neutrophil (heterophil) counts in synovium of untreated side (fellow) joints.

Sustained release Dex:HA gel suspensions exerted a local effect on the treated joint only and did not decrease inflammation in the contra-lateral (untreated) knee joint (FIG. 5B). These data show that administration of Dex:HA gel suspension to the infrapatellar fat pad does not cause systemic exposure within the therapeutically effective range. However, infrapatellar fat pat injection (IF) or intra-articular injection (IA) of Dex (positive control) at Day −1 yielded a bi-lateral reduction in inflammation (FIG. 5B); this finding indicates that this standard of care formulation (Dex) reached systemic levels in the therapeutically effective range.

As shown in FIG. 6, the infrapatellar fat pad is a favorable site for delivering sustained release drug to the synovium. Pharmacokinetic analysis of blood, synovial fluid and fat pad showed that infrapatellar fat pad delivery of Dex:HA gel suspension was sufficient to deliver sustained levels of drug to synovial tissues of rabbits with joint inflammation for at least 8 days, and lasted much longer than a single injection of Dex, which was not detectable in the synovial fluid after 2 days following injection. Most importantly, drug concentration in the synovial fluid was approximately 20 to several hundred-fold higher than the concentrations in plasma and contralateral joint. This indicates enriched localization of drug at the disease site, with minimal systemic exposure (FIG. 6).

Collectively, these results demonstrate a local fat pad injection of sustained release Dex:HA is effective in reducing the severity of synovial joint inflammation, and provides sustainable and similar efficacy to an intra-articular injection of Dex with minimal systemic exposure.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, those skilled in the art could make numerous and various modifications or changes to or alternative configurations of the disclosed subject matter can be made in accordance with the teachings herein without departing from the spirit of the present specification. Changes in detail may be made without departing from the spirit of the invention as defined in the appended claims. Lastly, the terminology used herein is for the purpose of describing particular embodiments only, and is not intended to limit the scope of the present invention, which is defined solely by the claims. In addition, it is intended that all matter contained in the above description or shown in the accompanying drawings shall be interpreted as illustrative only and not limiting. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

What is claimed is:

1. A method of treating pain, inflammation, or a combination thereof, in a joint of a subject in need of such treatment, the method comprising administering a gel suspension formulation into a fat pad of the joint, thereby relieving the joint from the pain, inflammation, or combination thereof;

wherein the formulation comprises:
   a non-crosslinked hyaluronic acid present at a concentration ranging from 2% to 10% (wt/wt) of the formulation; and
   dexamethasone, or a salt thereof, which is suspended in the formulation and present at a concentration ranging from 0.1% to 50% (wt/wt) of the formulation;
wherein the formulation provides sustained release of the dexamethasone, or the salt thereof, to the joint;
wherein the method provides consisting of reduced systemic exposure relative to a systemic or an intra-articular administration of a therapeutic dose of dexamethasone; and
wherein a single administration of the formulation to the joint fat pad provides equivalent or superior relief of the pain or inflammation of the joint relative to a single systemic or intra-articular administration of a therapeutic dose of dexamethasone; and
wherein the administering comprises injecting, embedding or implanting the formulation into the joint fat pad.

2. The method of claim 1 wherein the dexamethasone, or the salt thereof, is present at a concentration ranging from 0.5% to 30% (wt/wt) of the formulation.

3. The method of claim 1, wherein the hyaluronic acid is sodium hyaluronan.

4. The method of claim 1 wherein the hyaluronic acid is present at a concentration ranging from 2% to 5% (wt/wt) of the formulation.

5. The method of claim 1, wherein the formulation further comprises an anesthetic agent.

6. The method of claim 5, wherein the anesthetic agent is lidocaine.

7. The method of claim 1, wherein the joint is an arthritic joint, an injured joint or a surgically replaced joint.

8. The method of claim 1, wherein the joint is a synovial joint.

9. The method of claim 1, wherein the joint is a knee joint, and the fat pad is an infrapatellar fat pad.

10. The method of claim 1, wherein the pain, inflammation or the combination thereof is associated with osteoarthritis, rheumatoid arthritis, juvenile arthritis, calcium pyrophosphate dehydrate crystal deposition disease (pseudo gout), post-operative pain, joint replacement surgery pain or a combination thereof.

11. The method of claim 1, comprising a single injection of the gel formulation into the joint fat pad.

12. The method of claim 2, wherein the dexamethasone, or the salt thereof, is present at a concentration ranging from 1% to 25% (wt/wt) of the formulation.

13. The method of claim 2, wherein the dexamethasone, or the salt thereof, is present at a concentration ranging from 2% to 20% (wt/wt) of the formulation.

14. The method of claim 1, wherein the hyaluronic acid is present at a concentration of 2% (wt/wt) of the formulation, and the dexamethasone, or the salt thereof, is present at a concentration of 10% (wt/wt) of the formulation.

15. The method of claim 1, wherein: the formulation is a gel suspension; the dexamethasone, or the salt thereof, is present at a concentration ranging from 1% to 25% (wt/wt) of the formulation; the hyaluronic acid is present at a concentration ranging from 2% to 5% (wt/wt) of the formulation; and the formulation delivers pharmacodynamic concentrations of the dexamethasone to the joint for up to about 6 months after the administration.

16. The method of claim 1, wherein the hyaluronic acid is present at a concentration of 2% (wt/wt) of the formulation, and the dexamethasone, or the salt thereof, is present at a concentration of 20% (wt/wt) of the formulation.

* * * * *